United States Patent
Mazlish et al.

(10) Patent No.: US 11,929,158 B2
(45) Date of Patent: *Mar. 12, 2024

(54) USER INTERFACE FOR DIABETES MANAGEMENT SYSTEM

(71) Applicant: Insulet Corporation, Acton, MA (US)

(72) Inventors: Bryan Mazlish, Palo Alto, CA (US); Jeffrey Brewer, Menlo Park, CA (US); Lane Desborough, Thousand Oaks, CA (US); Jennifer Block, Menlo Park, CA (US); Robert Weishar, Daly City, CA (US); Alan Schachtely, Dublin, CA (US)

(73) Assignee: Insulet Corporation, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/360,751

(22) Filed: Mar. 21, 2019

(65) Prior Publication Data

US 2019/0221307 A1 Jul. 18, 2019

Related U.S. Application Data

(63) Continuation of application No. 15/402,493, filed on Jan. 10, 2017, now Pat. No. 10,275,573.

(Continued)

(51) Int. Cl.
*G16H 20/17* (2018.01)
*A61M 5/142* (2006.01)
(Continued)

(52) U.S. Cl.
CPC ........ *G16H 20/17* (2018.01); *A61M 5/14244* (2013.01); *A61M 5/1723* (2013.01);
(Continued)

(58) Field of Classification Search
CPC ........ G16H 20/17; G16H 20/60; G06F 19/00; A61M 5/1723; A61M 2205/583; A61M 2230/201
See application file for complete search history.

(56) References Cited

U.S. PATENT DOCUMENTS 303,013 A 8/1884 Horton
445,545 A 2/1891 Crane
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — Bradley J Osinski
(74) *Attorney, Agent, or Firm* — TraskBritt

(57) ABSTRACT

A diabetes management system including a pump for dispensing a medicant and a control device for controlling the pump includes a user interface for controlling functions of the pump and providing information related to operation of the pump and other information. The user interface can display blood glucose information and insulin dosing data such that a user can appropriately act on the information and/or gain confidence that the diabetes management system is operating appropriately to manage the disease. User interfaces provided herein can include displays of current and projected glucose values, bolus calculators, charts displaying glucose levels and/or insulin delivery data, system maintenance reminders, system status information, patient configuration input screens, and log-in screens. Diabetes management systems can include insulin pumps, continuous glucose monitors, blood glucose monitors, mobile comput- (Continued)

ing devices, servers, and/or other insulin delivery devices (e.g., insulin pens).

27 Claims, 15 Drawing Sheets

Related U.S. Application Data

(60) Provisional application No. 62/278,231, filed on Jan. 13, 2016.

(51) Int. Cl.
*A61M 5/172* (2006.01)
*G16H 20/60* (2018.01)
*G16H 40/63* (2018.01)
*G16H 40/67* (2018.01)

(52) U.S. Cl.
CPC .............. *G16H 20/60* (2018.01); *G16H 40/63* (2018.01); *G16H 40/67* (2018.01); *A61M 2005/14208* (2013.01); *A61M 5/14276* (2013.01); *A61M 2005/14288* (2013.01); *A61M 2205/18* (2013.01); *A61M 2205/3303* (2013.01); *A61M 2205/3523* (2013.01); *A61M 2205/3569* (2013.01); *A61M 2205/3584* (2013.01); *A61M 2205/50* (2013.01); *A61M 2205/502* (2013.01); *A61M 2205/581* (2013.01); *A61M 2205/582* (2013.01); *A61M 2205/583* (2013.01); *A61M 2230/201* (2013.01)

(56) References Cited

U.S. PATENT DOCUMENTS

| | | |
|---|---|---|
| 588,583 A | 8/1897 | Lade |
| 1,441,508 A | 1/1923 | Marius et al. |
| 2,283,925 A | 5/1942 | Harvey |
| 2,797,149 A | 6/1957 | Skeggs |
| 2,886,529 A | 5/1959 | Guillaud |
| 3,413,573 A | 11/1968 | Nathanson et al. |
| 3,574,114 A | 4/1971 | Monforte |
| 3,614,554 A | 10/1971 | Shield et al. |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,885,662 A | 5/1975 | Schaefer |
| 3,963,380 A | 6/1976 | Thomas et al. |
| 3,983,077 A | 9/1976 | Fuller et al. |
| 4,055,175 A | 10/1977 | Clemens et al. |
| 4,108,177 A | 8/1978 | Pistor |
| 4,146,029 A | 3/1979 | Ellinwood, Jr. |
| 4,151,845 A | 5/1979 | Clemens |
| 4,245,634 A | 1/1981 | Albisser et al. |
| 4,268,150 A | 5/1981 | Chen |
| 4,295,176 A | 10/1981 | Wittwer |
| 4,313,439 A | 2/1982 | Babb et al. |
| 4,368,980 A | 1/1983 | Aldred et al. |
| 4,373,527 A | 2/1983 | Fischell |
| 4,400,683 A | 8/1983 | Eda et al. |
| 4,403,984 A | 9/1983 | Ash et al. |
| 4,424,720 A | 1/1984 | Bucchianeri |
| 4,435,173 A | 3/1984 | Siposs et al. |
| 4,464,170 A | 8/1984 | Clemens et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,523,170 A | 6/1985 | Huth, III |
| 4,526,568 A | 7/1985 | Clemens et al. |
| 4,526,569 A | 7/1985 | Bernardi |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,562,751 A | 1/1986 | Nason et al. |
| 4,573,968 A | 3/1986 | Parker |
| 4,585,439 A | 4/1986 | Michel |
| 4,601,707 A | 7/1986 | Albisser et al. |
| 4,624,661 A | 11/1986 | Arimond |
| 4,633,878 A | 1/1987 | Bombardieri |
| 4,634,427 A | 1/1987 | Hannula et al. |
| 4,646,038 A | 2/1987 | Wanat |
| 4,657,529 A | 4/1987 | Prince et al. |
| 4,678,408 A | 7/1987 | Nason et al. |
| 4,684,368 A | 8/1987 | Kenyon |
| 4,685,903 A | 8/1987 | Cable et al. |
| 4,731,726 A | 3/1988 | Allen, III |
| 4,743,243 A | 5/1988 | Vaillancourt |
| 4,755,169 A | 7/1988 | Sarnoff et al. |
| 4,755,173 A | 7/1988 | Konopka et al. |
| 4,759,120 A | 7/1988 | Bernstein |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,859,492 A | 8/1989 | Rogers et al. |
| 4,880,770 A | 11/1989 | Mir et al. |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,944,659 A | 7/1990 | Labbe et al. |
| 4,967,201 A | 10/1990 | Rich, III |
| 4,969,874 A | 11/1990 | Michel et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,007,458 A | 4/1991 | Marcus et al. |
| 5,061,424 A | 10/1991 | Karimi et al. |
| 5,062,841 A | 11/1991 | Siegel |
| 5,084,749 A | 1/1992 | Losee et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,130,675 A | 7/1992 | Sugawara |
| 5,134,079 A | 7/1992 | Cusack et al. |
| 5,139,999 A | 8/1992 | Gordon et al. |
| 5,153,827 A | 10/1992 | Coutre et al. |
| 5,154,973 A | 10/1992 | Imagawa et al. |
| 5,165,406 A | 11/1992 | Wong |
| 5,176,662 A | 1/1993 | Bartholomew et al. |
| 5,178,609 A | 1/1993 | Ishikawa |
| 5,189,609 A | 2/1993 | Tivig et al. |
| 5,198,824 A | 3/1993 | Poradish |
| 5,205,819 A | 4/1993 | Ross et al. |
| 5,207,642 A | 5/1993 | Orkin et al. |
| 5,213,483 A | 5/1993 | Flaherty et al. |
| 5,217,754 A | 6/1993 | Santiago-Aviles et al. |
| 5,219,377 A | 6/1993 | Poradish |
| 5,232,439 A | 8/1993 | Campbell et al. |
| 5,237,993 A | 8/1993 | Skrabal |
| 5,244,463 A | 9/1993 | Cordner et al. |
| 5,254,096 A | 10/1993 | Rondelet et al. |
| 5,257,980 A | 11/1993 | Van et al. |
| 5,261,882 A | 11/1993 | Sealfon |
| 5,263,198 A | 11/1993 | Geddes et al. |
| 5,272,485 A | 12/1993 | Mason et al. |
| 5,273,517 A | 12/1993 | Barone et al. |
| 5,281,202 A | 1/1994 | Weber et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,346,476 A | 9/1994 | Elson |

(56) References Cited

U.S. PATENT DOCUMENTS

| | | | |
|---|---|---|---|
| 5,364,342 | A | 11/1994 | Beuchat et al. |
| 5,377,674 | A | 1/1995 | Kuestner |
| 5,380,665 | A | 1/1995 | Cusack et al. |
| 5,385,539 | A | 1/1995 | Maynard |
| 5,389,078 | A | 2/1995 | Zalesky et al. |
| 5,403,797 | A | 4/1995 | Ohtani et al. |
| 5,411,889 | A | 5/1995 | Hoots et al. |
| 5,421,812 | A | 6/1995 | Langley et al. |
| 5,427,988 | A | 6/1995 | Sengupta et al. |
| 5,433,710 | A | 7/1995 | Vanantwerp et al. |
| 5,456,945 | A | 10/1995 | McMillan et al. |
| 5,468,727 | A | 11/1995 | Phillips et al. |
| 5,478,610 | A | 12/1995 | Desu et al. |
| 5,505,709 | A | 4/1996 | Funderburk et al. |
| 5,505,828 | A | 4/1996 | Wong et al. |
| 5,507,288 | A | 4/1996 | Boecker et al. |
| 5,513,382 | A | 4/1996 | Agahi-Kesheh et al. |
| 5,533,389 | A | 7/1996 | Kamen et al. |
| 5,535,445 | A | 7/1996 | Gunton |
| 5,540,772 | A | 7/1996 | McMillan et al. |
| 5,543,773 | A | 8/1996 | Evans et al. |
| 5,558,640 | A | 9/1996 | Pfeiler et al. |
| 5,569,186 | A | 10/1996 | Lord et al. |
| 5,582,593 | A | 12/1996 | Hultman |
| 5,584,053 | A | 12/1996 | Kommrusch et al. |
| 5,584,813 | A | 12/1996 | Livingston et al. |
| 5,590,387 | A | 12/1996 | Schmidt et al. |
| 5,609,572 | A | 3/1997 | Lang |
| 5,614,252 | A | 3/1997 | McMillan et al. |
| 5,625,365 | A | 4/1997 | Tom et al. |
| 5,635,433 | A | 6/1997 | Sengupta |
| 5,637,095 | A | 6/1997 | Nason et al. |
| 5,665,065 | A | 9/1997 | Colman et al. |
| 5,665,070 | A | 9/1997 | McPhee |
| 5,678,539 | A | 10/1997 | Schubert et al. |
| 5,685,844 | A | 11/1997 | Marttila |
| 5,685,859 | A | 11/1997 | Kornerup |
| 5,693,018 | A | 12/1997 | Kriesel et al. |
| 5,697,899 | A | 12/1997 | Hillman et al. |
| 5,700,695 | A | 12/1997 | Yassinzadeh et al. |
| 5,703,364 | A | 12/1997 | Rosenthal |
| 5,707,459 | A | 1/1998 | Itoyama et al. |
| 5,707,715 | A | 1/1998 | Derochemont et al. |
| 5,713,875 | A | 2/1998 | Tanner, II |
| 5,714,123 | A | 2/1998 | Sohrab |
| 5,716,343 | A | 2/1998 | Kriesel et al. |
| 5,722,397 | A | 3/1998 | Eppstein |
| 5,741,228 | A | 4/1998 | Lambrecht et al. |
| 5,746,217 | A | 5/1998 | Erickson et al. |
| 5,747,350 | A | 5/1998 | Sattler |
| 5,747,870 | A | 5/1998 | Pedder |
| 5,748,827 | A | 5/1998 | Holl et al. |
| 5,755,682 | A | 5/1998 | Knudson et al. |
| 5,758,643 | A | 6/1998 | Wong et al. |
| 5,759,923 | A | 6/1998 | McMillan et al. |
| 5,764,189 | A | 6/1998 | Lohninger |
| 5,771,567 | A | 6/1998 | Pierce et al. |
| 5,776,103 | A | 7/1998 | Kriesel et al. |
| 5,779,676 | A | 7/1998 | Kriesel et al. |
| 5,785,688 | A | 7/1998 | Joshi et al. |
| 5,797,881 | A | 8/1998 | Gadot |
| 5,800,397 | A | 9/1998 | Wilson et al. |
| 5,800,405 | A | 9/1998 | McPhee |
| 5,800,420 | A | 9/1998 | Gross et al. |
| 5,801,057 | A | 9/1998 | Smart et al. |
| 5,804,048 | A | 9/1998 | Wong et al. |
| 5,807,075 | A | 9/1998 | Jacobsen et al. |
| 5,817,007 | A | 10/1998 | Fodgaard et al. |
| 5,820,622 | A | 10/1998 | Gross et al. |
| 5,823,951 | A | 10/1998 | Messerschmidt |
| 5,839,467 | A | 11/1998 | Saaski et al. |
| 5,840,020 | A | 11/1998 | Heinonen et al. |
| D403,313 | S | 12/1998 | Peppel |
| 5,848,991 | A | 12/1998 | Gross et al. |
| 5,851,197 | A | 12/1998 | Marano et al. |
| 5,854,608 | A | 12/1998 | Leisten |
| 5,858,005 | A | 1/1999 | Kriesel |
| 5,858,239 | A | 1/1999 | Kenley et al. |
| 5,859,621 | A | 1/1999 | Leisten |
| 5,865,806 | A | 2/1999 | Howell |
| 5,871,470 | A | 2/1999 | McWha |
| 5,879,310 | A | 3/1999 | Sopp et al. |
| 5,889,459 | A | 3/1999 | Hattori et al. |
| 5,891,097 | A | 4/1999 | Saito et al. |
| 5,892,489 | A | 4/1999 | Kanba et al. |
| 5,897,530 | A | 4/1999 | Jackson |
| 5,902,253 | A | 5/1999 | Pfeiffer et al. |
| 5,903,421 | A | 5/1999 | Furutani et al. |
| 5,906,597 | A | 5/1999 | McPhee |
| 5,911,716 | A | 6/1999 | Rake et al. |
| 5,919,167 | A | 7/1999 | Mulhauser et al. |
| 5,931,814 | A | 8/1999 | Alex et al. |
| 5,932,175 | A | 8/1999 | Knute et al. |
| 5,933,121 | A | 8/1999 | Rainhart et al. |
| 5,935,099 | A | 8/1999 | Peterson et al. |
| 5,945,963 | A | 8/1999 | Leisten |
| 5,947,911 | A | 9/1999 | Wong et al. |
| 5,957,890 | A | 9/1999 | Mann et al. |
| 5,961,492 | A | 10/1999 | Kriesel et al. |
| 5,965,848 | A | 10/1999 | Altschul et al. |
| 5,971,941 | A | 10/1999 | Simons et al. |
| 5,993,423 | A | 11/1999 | Choi |
| 5,997,501 | A | 12/1999 | Gross et al. |
| 6,005,151 | A | 12/1999 | Herrmann et al. |
| 6,017,318 | A | 1/2000 | Gauthier et al. |
| 6,019,747 | A | 2/2000 | McPhee |
| 6,023,251 | A | 2/2000 | Koo et al. |
| 6,024,539 | A | 2/2000 | Blomquist |
| 6,027,826 | A | 2/2000 | Derochemont et al. |
| 6,028,568 | A | 2/2000 | Asakura et al. |
| 6,031,445 | A | 2/2000 | Marty et al. |
| 6,032,059 | A | 2/2000 | Henning et al. |
| 6,036,924 | A | 3/2000 | Simons et al. |
| 6,040,578 | A | 3/2000 | Malin et al. |
| 6,040,805 | A | 3/2000 | Huynh et al. |
| 6,046,707 | A | 4/2000 | Gaughan et al. |
| 6,049,727 | A | 4/2000 | Crothall |
| 6,050,978 | A | 4/2000 | Orr et al. |
| 6,052,040 | A | 4/2000 | Hino |
| 6,058,934 | A | 5/2000 | Sullivan |
| 6,066,103 | A | 5/2000 | Duchon et al. |
| 6,071,292 | A | 6/2000 | Makower et al. |
| 6,072,180 | A | 6/2000 | Kramer et al. |
| 6,077,055 | A | 6/2000 | Scott |
| 6,090,092 | A | 7/2000 | Fowles et al. |
| 6,101,406 | A | 8/2000 | Hacker et al. |
| 6,102,872 | A | 8/2000 | Doneen et al. |
| 6,111,544 | A | 8/2000 | Dakeya et al. |
| 6,115,673 | A | 9/2000 | Malin et al. |
| 6,123,827 | A | 9/2000 | Wong et al. |
| 6,124,134 | A | 9/2000 | Stark |
| 6,126,637 | A | 10/2000 | Kriesel et al. |
| 6,128,519 | A | 10/2000 | Say |
| 6,142,939 | A | 11/2000 | Eppstein et al. |
| 6,143,164 | A | 11/2000 | Heller et al. |
| 6,143,432 | A | 11/2000 | De et al. |
| 6,154,176 | A | 11/2000 | Fathy et al. |
| 6,157,041 | A | 12/2000 | Thomas et al. |
| 6,161,028 | A | 12/2000 | Braig et al. |
| 6,162,639 | A | 12/2000 | Douglas |
| 6,174,300 | B1 | 1/2001 | Kriesel et al. |
| 6,176,004 | B1 | 1/2001 | Rainhart et al. |
| 6,181,297 | B1 | 1/2001 | Leisten |
| 6,188,368 | B1 | 2/2001 | Koriyama et al. |
| 6,190,359 | B1 | 2/2001 | Heruth |
| 6,195,049 | B1 | 2/2001 | Kim et al. |
| 6,196,046 | B1 | 3/2001 | Braig et al. |
| 6,200,287 | B1 | 3/2001 | Keller et al. |
| 6,200,293 | B1 | 3/2001 | Kriesel et al. |
| 6,200,338 | B1 | 3/2001 | Solomon et al. |
| 6,204,203 | B1 | 3/2001 | Narwankar et al. |
| 6,208,843 | B1 | 3/2001 | Huang et al. |
| 6,214,629 | B1 | 4/2001 | Freitag et al. |
| 6,222,489 | B1 | 4/2001 | Tsuru et al. |

(56) References Cited

U.S. PATENT DOCUMENTS

| | | |
|---|---|---|
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,266,020 B1 | 7/2001 | Chang |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,300,894 B1 | 10/2001 | Lynch et al. |
| 6,309,370 B1 | 10/2001 | Ben-Haim et al. |
| 6,312,888 B1 | 11/2001 | Wong et al. |
| 6,320,547 B1 | 11/2001 | Fathy et al. |
| 6,323,549 B1 | 11/2001 | Derochemont et al. |
| 6,334,851 B1 | 1/2002 | Hayes et al. |
| 6,363,609 B1 | 4/2002 | Pickren |
| 6,375,627 B1 | 4/2002 | Mauze et al. |
| 6,375,638 B2 | 4/2002 | Nason et al. |
| 6,379,301 B1 | 4/2002 | Worthington et al. |
| 6,402,689 B1 | 6/2002 | Scarantino et al. |
| 6,413,244 B1 | 7/2002 | Bestetti et al. |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Viana et al. |
| 6,512,937 B2 | 1/2003 | Blank et al. |
| 6,520,936 B1 | 2/2003 | Mann |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,537,249 B2 | 3/2003 | Kriesell et al. |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,546,268 B1 | 4/2003 | Ishikawa et al. |
| 6,546,269 B1 | 4/2003 | Kurnik |
| 6,552,693 B1 | 4/2003 | Leisten |
| 6,553,841 B1 | 4/2003 | Blouch |
| 6,554,798 B1 | 4/2003 | Mann et al. |
| 6,556,850 B1 | 4/2003 | Braig et al. |
| D474,778 S | 5/2003 | Barnes |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,115 B1 | 5/2003 | Barker et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,583,699 B2 | 6/2003 | Yokoyama |
| 6,595,956 B1 | 7/2003 | Gross et al. |
| 6,611,419 B1 | 8/2003 | Chakravorty |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,642,908 B2 | 11/2003 | Pleva et al. |
| 6,645,142 B2 | 11/2003 | Braig et al. |
| 6,650,303 B2 | 11/2003 | Kim et al. |
| 6,653,091 B1 | 11/2003 | Dunn et al. |
| 6,656,158 B2 | 12/2003 | Mahoney et al. |
| 6,662,030 B2 | 12/2003 | Khalil et al. |
| 6,669,663 B1 | 12/2003 | Thompson |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,686,406 B2 | 2/2004 | Tomomatsu et al. |
| 6,690,336 B1 | 2/2004 | Leisten et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,890 B2 | 5/2004 | Imanaka et al. |
| 6,740,059 B2 | 5/2004 | Flaherty |
| 6,740,072 B2 | 5/2004 | Starkweather et al. |
| 6,741,148 B2 | 5/2004 | Killen et al. |
| 6,742,249 B2 | 6/2004 | Derochemont et al. |
| 6,743,744 B1 | 6/2004 | Kim et al. |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,753,745 B2 | 6/2004 | Killen et al. |
| 6,753,814 B2 | 6/2004 | Killen et al. |
| 6,758,835 B2 | 7/2004 | Close et al. |
| 6,762,237 B2 | 7/2004 | Glatkowski et al. |
| 6,780,156 B2 | 8/2004 | Haueter et al. |
| 6,787,181 B2 | 9/2004 | Uchiyama et al. |
| 6,791,496 B1 | 9/2004 | Killen et al. |
| 6,810,290 B2 | 10/2004 | Lebel et al. |
| 6,826,031 B2 | 11/2004 | Nagai et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,853,288 B2 | 2/2005 | Ahn et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,878,871 B2 | 4/2005 | Scher et al. |
| 6,883,778 B1 | 4/2005 | Newton et al. |
| 6,890,291 B2 | 5/2005 | Robinson et al. |
| 6,905,989 B2 | 6/2005 | Ellis et al. |
| 6,906,674 B2 | 6/2005 | McKinzie et al. |
| 6,914,566 B2 | 7/2005 | Beard |
| 6,919,119 B2 | 7/2005 | Kalkan et al. |
| 6,928,298 B2 | 8/2005 | Furutani et al. |
| 6,936,029 B2 | 8/2005 | Mann et al. |
| 6,943,430 B2 | 9/2005 | Kwon |
| 6,943,731 B2 | 9/2005 | Killen et al. |
| 6,949,081 B1 | 9/2005 | Chance |
| 6,958,809 B2 | 10/2005 | Sterling et al. |
| 6,963,259 B2 | 11/2005 | Killen et al. |
| 6,989,891 B2 | 1/2006 | Braig et al. |
| 6,990,366 B2 | 1/2006 | Say et al. |
| 7,002,436 B2 | 2/2006 | Ma et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis et al. |
| 7,047,637 B2 | 5/2006 | Derochemont et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,096,124 B2 | 8/2006 | Sterling et al. |
| 7,115,205 B2 | 10/2006 | Robinson et al. |

(56) References Cited

U.S. PATENT DOCUMENTS

| | | |
|---|---|---|
| 7,116,949 B2 | 10/2006 | Irie et al. |
| 7,128,727 B2 | 10/2006 | Flaherty et al. |
| 7,137,694 B2 | 11/2006 | Ferran et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,160,272 B1 | 1/2007 | Eyal et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,230,316 B2 | 6/2007 | Yamazaki et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,291,782 B2 | 11/2007 | Sager et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,405,698 B2 | 7/2008 | De Rochemont |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van et al. |
| 7,500,949 B2 | 3/2009 | Gottlieb et al. |
| 7,509,156 B2 | 3/2009 | Flanders |
| D590,415 S | 4/2009 | Ball et al. |
| 7,522,124 B2 | 4/2009 | Smith et al. |
| 7,547,281 B2 | 6/2009 | Hayes et al. |
| 7,553,512 B2 | 6/2009 | Kodas et al. |
| 7,564,887 B2 | 7/2009 | Wang et al. |
| 7,569,030 B2 | 8/2009 | Lebel et al. |
| 7,595,623 B2 | 9/2009 | Bennett |
| 7,608,042 B2 | 10/2009 | Goldberger et al. |
| 7,651,845 B2 | 1/2010 | Doyle et al. |
| 7,652,901 B2 | 1/2010 | Kirchmeier et al. |
| 7,680,529 B2 | 3/2010 | Kroll |
| D614,634 S | 4/2010 | Nilsen |
| 7,714,794 B2 | 5/2010 | Tavassoli Hozouri |
| 7,734,323 B2 | 6/2010 | Blomquist et al. |
| 7,763,917 B2 | 7/2010 | De Rochemont |
| 7,766,829 B2 | 8/2010 | Sloan et al. |
| 7,771,391 B2 | 8/2010 | Carter |
| 7,785,258 B2 | 8/2010 | Braig et al. |
| 7,806,854 B2 | 10/2010 | Damiano et al. |
| 7,806,886 B2 | 10/2010 | Kanderian et al. |
| 7,812,774 B2 | 10/2010 | Friman et al. |
| 7,918,825 B2 | 4/2011 | O'Connor et al. |
| 7,946,985 B2 | 5/2011 | Mastrototaro et al. |
| D640,269 S | 6/2011 | Chen |
| 7,972,296 B2 | 7/2011 | Braig et al. |
| 8,066,805 B2 | 11/2011 | Zuercher et al. |
| 8,069,690 B2 | 12/2011 | Desantolo et al. |
| 8,114,489 B2 | 2/2012 | Nemat-Nasser et al. |
| 8,178,457 B2 | 5/2012 | De Rochemont |
| 8,193,873 B2 | 6/2012 | Kato et al. |
| 8,221,345 B2 | 7/2012 | Blomquist |
| 8,251,907 B2 | 8/2012 | Sterling et al. |
| 8,267,921 B2 | 9/2012 | Yodfat et al. |
| 8,350,657 B2 | 1/2013 | Derochemont |
| 8,354,294 B2 | 1/2013 | De et al. |
| D677,685 S | 3/2013 | Simmons et al. |
| 8,417,312 B2 * | 4/2013 | Kamath ............ A61B 5/14532 600/347 |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| D688,686 S | 8/2013 | Rhee et al. |
| 8,547,239 B2 | 10/2013 | Peatfield et al. |
| D693,837 S | 11/2013 | Bouchier |
| 8,593,819 B2 | 11/2013 | De Rochemont |
| D695,757 S | 12/2013 | Ray et al. |
| 8,597,274 B2 | 12/2013 | Sloan et al. |
| 8,622,988 B2 | 1/2014 | Hayter |
| 8,715,839 B2 | 5/2014 | De Rochemont |
| D710,879 S | 8/2014 | Elston et al. |
| 8,810,394 B2 | 8/2014 | Kalpin |
| D714,822 S | 10/2014 | Capua et al. |
| D715,315 S | 10/2014 | Wood |
| D715,815 S | 10/2014 | Bortman et al. |
| D718,779 S | 12/2014 | Hang et al. |
| D720,366 S | 12/2014 | Hiltunen et al. |
| D720,765 S | 1/2015 | Xie et al. |
| 8,939,935 B2 | 1/2015 | O'Connor et al. |
| D726,760 S | 4/2015 | Yokota et al. |
| D727,928 S | 4/2015 | Allison et al. |
| D730,378 S | 5/2015 | Xiong et al. |
| D733,175 S | 6/2015 | Bae |
| 9,061,097 B2 | 6/2015 | Holt et al. |
| D734,356 S | 7/2015 | Xiong et al. |
| D736,811 S | 8/2015 | Teichner et al. |
| D737,305 S | 8/2015 | Scazafavo et al. |
| D737,831 S | 9/2015 | Lee |
| D737,832 S | 9/2015 | Lim et al. |
| D738,901 S | 9/2015 | Amin |
| D740,301 S | 10/2015 | Soegiono et al. |
| D740,308 S | 10/2015 | Kim et al. |
| D740,311 S | 10/2015 | Drozd et al. |
| D741,354 S | 10/2015 | Lee et al. |
| D741,359 S | 10/2015 | Ji-Hye et al. |
| 9,171,343 B1 | 10/2015 | Fischell et al. |
| D743,431 S | 11/2015 | Pal et al. |
| D743,991 S | 11/2015 | Pal et al. |
| 9,180,224 B2 | 11/2015 | Moseley et al. |
| 9,180,244 B2 | 11/2015 | Anderson et al. |
| 9,192,716 B2 | 11/2015 | Jugl et al. |
| D744,514 S | 12/2015 | Shin et al. |
| D744,517 S | 12/2015 | Pal et al. |
| D745,032 S | 12/2015 | Pal et al. |
| D745,034 S | 12/2015 | Pal et al. |
| D745,035 S | 12/2015 | Pal et al. |
| D746,827 S | 1/2016 | Jung et al. |
| D746,828 S | 1/2016 | Arai et al. |
| D747,352 S | 1/2016 | Lee et al. |
| 9,233,204 B2 | 1/2016 | Booth et al. |
| D749,097 S | 2/2016 | Zou et al. |
| D749,118 S | 2/2016 | Wang |
| D751,100 S | 3/2016 | Lindn et al. |
| D752,604 S | 3/2016 | Zhang |
| D753,134 S | 4/2016 | Vazquez |
| D754,718 S | 4/2016 | Zhou |
| D755,193 S | 5/2016 | Sun et al. |
| D755,799 S | 5/2016 | Finnis et al. |
| D755,820 S | 5/2016 | Wang |
| D756,387 S | 5/2016 | Chang et al. |
| D757,032 S | 5/2016 | Sabia et al. |
| D757,035 S | 5/2016 | Raskin et al. |
| D758,391 S | 6/2016 | Suarez |
| D758,422 S | 6/2016 | Zhao |
| D759,032 S | 6/2016 | Amin et al. |
| D759,078 S | 6/2016 | Iwamoto |
| D759,678 S | 6/2016 | Jung et al. |
| D759,687 S | 6/2016 | Chang et al. |
| D761,812 S | 7/2016 | Motamedi |
| D763,308 S | 8/2016 | Wang et al. |
| D763,868 S | 8/2016 | Lee et al. |
| D765,110 S | 8/2016 | Liang |
| D765,124 S | 8/2016 | Minks-Brown et al. |
| 9,402,950 B2 | 8/2016 | Dilanni et al. |
| D765,707 S | 9/2016 | Gomez |
| D766,286 S | 9/2016 | Lee et al. |
| D767,586 S | 9/2016 | Kwon et al. |
| D768,154 S | 10/2016 | Kim et al. |
| D768,188 S | 10/2016 | Li et al. |
| D768,660 S | 10/2016 | Wielgosz |
| D768,685 S | 10/2016 | Lee et al. |

(56) References Cited

U.S. PATENT DOCUMENTS

| | | |
|---|---|---|
| D769,315 S | 10/2016 | Scotti |
| D770,507 S | 11/2016 | Umezawa et al. |
| D770,515 S | 11/2016 | Cho et al. |
| D771,073 S | 11/2016 | Choi et al. |
| D771,076 S | 11/2016 | Butcher et al. |
| D771,690 S | 11/2016 | Yin et al. |
| D772,911 S | 11/2016 | Lee et al. |
| 9,486,571 B2 | 11/2016 | Rosinko |
| D773,531 S | 12/2016 | Toth et al. |
| D775,184 S | 12/2016 | Song et al. |
| D775,196 S | 12/2016 | Huang et al. |
| 9,520,649 B2 | 12/2016 | De Rochemont |
| D775,658 S | 1/2017 | Luo et al. |
| D776,126 S | 1/2017 | Lai et al. |
| D776,687 S | 1/2017 | Wick et al. |
| D777,191 S | 1/2017 | Polimeni |
| D777,758 S | 1/2017 | Kisselev et al. |
| 9,579,456 B2 | 2/2017 | Budiman et al. |
| D781,323 S | 3/2017 | Green et al. |
| D781,781 S | 3/2017 | Schimmoeller, Jr. |
| D781,877 S | 3/2017 | Ko et al. |
| D781,878 S | 3/2017 | Butcher et al. |
| D781,879 S | 3/2017 | Butcher et al. |
| D781,903 S | 3/2017 | Reichle et al. |
| D781,905 S | 3/2017 | Nakaguchi et al. |
| D782,506 S | 3/2017 | Kim et al. |
| D783,672 S | 4/2017 | Rajasankar et al. |
| D785,010 S | 4/2017 | Bachman et al. |
| D785,656 S | 5/2017 | Bramer et al. |
| D786,278 S | 5/2017 | Motamedi |
| D786,898 S | 5/2017 | Hall |
| D788,126 S | 5/2017 | Evnin et al. |
| 9,656,017 B2 | 5/2017 | Greene |
| D788,621 S | 6/2017 | Shallice et al. |
| D788,652 S | 6/2017 | Mutsuro et al. |
| D789,402 S | 6/2017 | Dye et al. |
| D789,967 S | 6/2017 | Kaplan et al. |
| D789,982 S | 6/2017 | Christiana et al. |
| D790,560 S | 6/2017 | Inose et al. |
| D791,781 S | 7/2017 | Donarski et al. |
| D791,805 S | 7/2017 | Segars |
| D791,812 S | 7/2017 | Bistoni et al. |
| D793,412 S | 8/2017 | Chaudhri et al. |
| D795,886 S | 8/2017 | Ng et al. |
| D795,891 S | 8/2017 | Kohan et al. |
| D795,900 S | 8/2017 | Bischoff et al. |
| D795,906 S | 8/2017 | Butrick |
| D795,927 S | 8/2017 | Bischoff et al. |
| 9,743,224 B2 | 8/2017 | San et al. |
| D796,530 S | 9/2017 | McMillan et al. |
| D796,540 S | 9/2017 | McLean et al. |
| D797,116 S | 9/2017 | Chapman et al. |
| D797,763 S | 9/2017 | Kim et al. |
| D797,774 S | 9/2017 | Park et al. |
| D797,797 S | 9/2017 | Gandhi et al. |
| D798,310 S | 9/2017 | Golden et al. |
| D798,311 S | 9/2017 | Golden et al. |
| D799,536 S | 10/2017 | Eder |
| D800,765 S | 10/2017 | Stoksik |
| D800,769 S | 10/2017 | Hennessy et al. |
| D801,383 S | 10/2017 | Park et al. |
| D802,011 S | 11/2017 | Friedman et al. |
| D802,088 S | 11/2017 | Bos et al. |
| D803,232 S | 11/2017 | Leigh et al. |
| D803,242 S | 11/2017 | Mizono et al. |
| D804,502 S | 12/2017 | Amini et al. |
| D805,525 S | 12/2017 | Dascola et al. |
| D806,716 S | 1/2018 | Pahwa et al. |
| D807,376 S | 1/2018 | Mizono et al. |
| D807,400 S | 1/2018 | Lagreca |
| D807,910 S | 1/2018 | Graham et al. |
| D807,918 S | 1/2018 | Cohen et al. |
| D807,919 S | 1/2018 | Cohen et al. |
| D808,423 S | 1/2018 | Jiang et al. |
| D808,974 S | 1/2018 | Chiappone et al. |
| D808,983 S | 1/2018 | Narinedhat et al. |
| 9,857,090 B2 | 1/2018 | Golden et al. |
| D810,116 S | 2/2018 | McLean et al. |
| D810,771 S | 2/2018 | Gandhi et al. |
| 9,907,515 B2 | 3/2018 | Doyle et al. |
| D815,131 S | 4/2018 | Thompson et al. |
| D816,090 S | 4/2018 | Stonecipher et al. |
| D817,339 S | 5/2018 | Nanjappan et al. |
| D818,491 S | 5/2018 | Timmer et al. |
| D819,057 S | 5/2018 | Huang |
| D819,059 S | 5/2018 | O'Toole |
| 9,980,140 B1 | 5/2018 | Spencer et al. |
| 9,984,773 B2 | 5/2018 | Gondhalekar et al. |
| D820,311 S | 6/2018 | Cabrera et al. |
| D820,862 S | 6/2018 | Alfonzo et al. |
| D822,034 S | 7/2018 | Clymer et al. |
| D822,677 S | 7/2018 | Weaver et al. |
| D822,684 S | 7/2018 | Clausen-Stuck et al. |
| D822,692 S | 7/2018 | Loychik et al. |
| D823,862 S | 7/2018 | Chung et al. |
| D824,400 S | 7/2018 | Chang et al. |
| D824,951 S | 8/2018 | Kolbrener et al. |
| D826,956 S | 8/2018 | Pillalamarri et al. |
| D826,957 S | 8/2018 | Pillalamarri et al. |
| D828,381 S | 9/2018 | Lee et al. |
| D829,732 S | 10/2018 | Jeffrey et al. |
| D830,374 S | 10/2018 | Leonard et al. |
| D830,384 S | 10/2018 | Lepine et al. |
| D830,385 S | 10/2018 | Lepine et al. |
| D830,407 S | 10/2018 | Kisielius et al. |
| D831,033 S | 10/2018 | Leonard et al. |
| D833,469 S | 11/2018 | Coleman et al. |
| D834,601 S | 11/2018 | Felt |
| D835,132 S | 12/2018 | Ito et al. |
| D835,145 S | 12/2018 | Cashner et al. |
| D835,147 S | 12/2018 | Kisielius et al. |
| D835,651 S | 12/2018 | Bao |
| D835,666 S | 12/2018 | Saleh et al. |
| D836,123 S | 12/2018 | Pillalamarri et al. |
| D837,807 S | 1/2019 | Baber et al. |
| D838,731 S | 1/2019 | Pillalamarri et al. |
| D840,418 S | 2/2019 | Saad et al. |
| D840,419 S | 2/2019 | Saad et al. |
| D844,022 S | 3/2019 | Amin |
| D845,317 S | 4/2019 | Wellmeier et al. |
| 10,248,839 B2 | 4/2019 | Levy et al. |
| D848,459 S | 5/2019 | Li |
| D851,099 S | 6/2019 | Uppala et al. |
| D851,658 S | 6/2019 | Pillalamarri et al. |
| 10,335,464 B1 | 7/2019 | Michelich et al. |
| D865,795 S | 11/2019 | Koo |
| D872,746 S | 1/2020 | Laborde |
| D874,471 S | 2/2020 | Pillalamarri et al. |
| D875,114 S | 2/2020 | Clediere |
| 10,583,250 B2 | 3/2020 | Mazlish et al. |
| D880,498 S | 4/2020 | Shahidi et al. |
| D888,070 S | 6/2020 | Yusupov et al. |
| 10,737,024 B2 | 8/2020 | Schmid |
| D904,426 S | 12/2020 | Paul |
| D911,353 S | 2/2021 | Sanchez et al. |
| D914,031 S | 3/2021 | Ding et al. |
| D916,729 S | 4/2021 | Gabriel et al. |
| D916,870 S | 4/2021 | Hemsley |
| D916,878 S | 4/2021 | Kim et al. |
| 10,987,468 B2 | 4/2021 | Mazlish et al. |
| D918,261 S | 5/2021 | Ramamurthy et al. |
| D920,351 S | 5/2021 | Zhang |
| D923,033 S | 6/2021 | Smith et al. |
| D927,533 S | 8/2021 | Clymer |
| D938,447 S | 12/2021 | Holland |
| 11,197,964 B2 | 12/2021 | Sjolund et al. |
| 11,260,169 B2 | 3/2022 | Estes |
| D954,078 S | 6/2022 | Rahate et al. |
| 2001/0021803 A1 | 9/2001 | Blank et al. |
| 2001/0034023 A1 | 10/2001 | Stanton et al. |
| 2001/0034502 A1 | 10/2001 | Moberg et al. |
| 2001/0048969 A1 | 12/2001 | Constantino et al. |
| 2001/0051377 A1 | 12/2001 | Hammer et al. |
| 2001/0053895 A1 | 12/2001 | Vaillancourt |

(56) References Cited

U.S. PATENT DOCUMENTS

| | | |
|---|---|---|
| 2001/0056258 A1 | 12/2001 | Evans |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0047768 A1 | 4/2002 | Duffy |
| 2002/0070983 A1 | 6/2002 | Kozub et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0173769 A1 | 11/2002 | Gray et al. |
| 2002/0190818 A1 | 12/2002 | Endou et al. |
| 2003/0023148 A1 | 1/2003 | Lorenz et al. |
| 2003/0023152 A1 | 1/2003 | Abbink et al. |
| 2003/0034124 A1 | 2/2003 | Sugaya et al. |
| 2003/0040715 A1 | 2/2003 | D'Antonio et al. |
| 2003/0050621 A1 | 3/2003 | Lebel et al. |
| 2003/0060692 A1 | 3/2003 | Ruchti et al. |
| 2003/0086073 A1 | 5/2003 | Braig et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0122647 A1 | 7/2003 | Ou |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0170436 A1 | 9/2003 | Sumi et al. |
| 2003/0175806 A1 | 9/2003 | Rule et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman et al. |
| 2003/0221621 A1 | 12/2003 | Pokharna et al. |
| 2004/0001027 A1 | 1/2004 | Killen et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064259 A1 | 4/2004 | Haaland et al. |
| 2004/0068224 A1 | 4/2004 | Couvillon et al. |
| 2004/0069004 A1 | 4/2004 | Gist et al. |
| 2004/0069044 A1 | 4/2004 | Lavi et al. |
| 2004/0087904 A1 | 5/2004 | Langley et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0134609 A1 | 6/2005 | Yu |
| 2005/0137573 A1 | 6/2005 | McLaughlin |
| 2005/0171503 A1 | 8/2005 | Van et al. |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Diianni et al. |
| 2005/0261660 A1 | 11/2005 | Choi |
| 2005/0262451 A1 | 11/2005 | Remignanti et al. |
| 2005/0272640 A1 | 12/2005 | Doyle et al. |
| 2005/0277912 A1 | 12/2005 | John |
| 2006/0009727 A1 | 1/2006 | O'Mahony et al. |
| 2006/0041229 A1 | 2/2006 | Garibotto et al. |
| 2006/0064053 A1 | 3/2006 | Bollish et al. |
| 2006/0079765 A1 | 4/2006 | Neer et al. |
| 2006/0079809 A1 | 4/2006 | Goldberger et al. |
| 2006/0086994 A1 | 4/2006 | Viefers et al. |
| 2006/0100494 A1 | 5/2006 | Kroll |
| 2006/0134323 A1 | 6/2006 | O'Brien |
| 2006/0134491 A1 | 6/2006 | Hilchenko et al. |
| 2006/0167350 A1 | 7/2006 | Monfre et al. |
| 2006/0173406 A1 | 8/2006 | Hayes et al. |
| 2006/0178633 A1 | 8/2006 | Garibotto et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0272652 A1 | 12/2006 | Stocker et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0100635 A1 | 5/2007 | Mahajan et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0166453 A1 | 7/2007 | Van et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0033320 A1 | 2/2008 | Racchini et al. |
| 2008/0051738 A1 | 2/2008 | Griffin |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0071580 A1* | 3/2008 | Marcus ............. G16H 15/00 705/3 |
| 2008/0078400 A1 | 4/2008 | Martens et al. |
| 2008/0097289 A1 | 4/2008 | Steil et al. |
| 2008/0114304 A1 | 5/2008 | Nalesso et al. |
| 2008/0132880 A1 | 6/2008 | Buchman |
| 2008/0160492 A1 | 7/2008 | Campbell et al. |
| 2008/0161664 A1 | 7/2008 | Mastrototaro et al. |
| 2008/0172026 A1 | 7/2008 | Blomquist |
| 2008/0172028 A1 | 7/2008 | Blomquist |

(56) References Cited

U.S. PATENT DOCUMENTS

| | | |
|---|---|---|
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0212966 A1 | 8/2009 | Panduro |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2009/0326472 A1 | 12/2009 | Carter et al. |
| 2010/0017141 A1 | 1/2010 | Campbell et al. |
| 2010/0036326 A1 | 2/2010 | Matusch |
| 2010/0057042 A1 | 3/2010 | Hayter |
| 2010/0064243 A1 | 3/2010 | Buck et al. |
| 2010/0077198 A1 | 3/2010 | Buck et al. |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0174228 A1 | 7/2010 | Buckingham et al. |
| 2010/0185183 A1 | 7/2010 | Alme et al. |
| 2010/0211003 A1 | 8/2010 | Sundar et al. |
| 2010/0228110 A1 | 9/2010 | Tsoukalis |
| 2010/0241066 A1 | 9/2010 | Hansen et al. |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2010/0305965 A1* | 12/2010 | Benjamin ............... G16H 15/00 |
| | | 705/2 |
| 2011/0021584 A1 | 1/2011 | Berggren et al. |
| 2011/0028817 A1 | 2/2011 | Jin et al. |
| 2011/0049394 A1 | 3/2011 | De Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071765 A1 | 3/2011 | Yodfat et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0124521 A1 | 5/2012 | Guo |
| 2012/0136336 A1 | 5/2012 | Mastrototaro et al. |
| 2012/0150446 A1 | 6/2012 | Chang et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0250449 A1 | 10/2012 | Nakano |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian et al. |
| 2013/0172695 A1 | 7/2013 | Nielsen et al. |
| 2013/0172710 A1* | 7/2013 | Mears ............... A61M 5/14244 |
| | | 600/365 |
| 2013/0178791 A1 | 7/2013 | Javitt |
| 2013/0231642 A1 | 9/2013 | Doyle et al. |
| 2013/0245545 A1 | 9/2013 | Arnold et al. |
| 2013/0253472 A1 | 9/2013 | Cabiri |
| 2013/0261406 A1 | 10/2013 | Rebec et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0332874 A1 | 12/2013 | Rosinko et al. |
| 2013/0338576 A1 | 12/2013 | O'Connor et al. |
| 2013/0346858 A1 | 12/2013 | Neyrinck |
| 2014/0005633 A1 | 1/2014 | Finan |
| 2014/0018730 A1 | 1/2014 | Mueller-Pathle |
| 2014/0032549 A1 | 1/2014 | McDaniel et al. |
| 2014/0066859 A1 | 3/2014 | Ogawa et al. |
| 2014/0066886 A1 | 3/2014 | Roy et al. |
| 2014/0074033 A1 | 3/2014 | Sonderegger et al. |
| 2014/0088428 A1 | 3/2014 | Yang et al. |
| 2014/0108046 A1 | 4/2014 | Echeverria et al. |
| 2014/0121635 A1 | 5/2014 | Hayter |
| 2014/0127048 A1 | 5/2014 | Diianni et al. |
| 2014/0128705 A1 | 5/2014 | Mazlish |
| 2014/0128839 A1 | 5/2014 | Diianni et al. |
| 2014/0129951 A1 | 5/2014 | Amin et al. |
| 2014/0135880 A1 | 5/2014 | Baumgartner et al. |
| 2014/0142508 A1 | 5/2014 | Diianni et al. |
| 2014/0146202 A1 | 5/2014 | Boss et al. |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200426 A1* | 7/2014 | Taub ................... A61B 5/14532 |
| | | 600/347 |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025503 A1 | 1/2015 | Searle et al. |
| 2015/0041498 A1 | 2/2015 | Kakiuchi et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0165119 A1 | 6/2015 | Palerm et al. |
| 2015/0173674 A1 | 6/2015 | Hayes et al. |

(56) References Cited

U.S. PATENT DOCUMENTS

| | | |
|---|---|---|
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Vinna et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0301691 A1 | 10/2015 | Qin |
| 2015/0306314 A1 | 10/2015 | Doyle et al. |
| 2015/0331995 A1 | 11/2015 | Zhao et al. |
| 2015/0351671 A1 | 12/2015 | Vanslyke et al. |
| 2015/0351672 A1 | 12/2015 | Vanslyke et al. |
| 2015/0356250 A1 | 12/2015 | Polimeni |
| 2015/0366945 A1 | 12/2015 | Greene |
| 2016/0015891 A1 | 1/2016 | Papiorek |
| 2016/0019352 A1 | 1/2016 | Cohen et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0220181 A1 | 8/2016 | Rigoard et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0007882 A1 | 1/2017 | Werner |
| 2017/0021096 A1 | 1/2017 | Cole et al. |
| 2017/0049386 A1 | 2/2017 | Abraham et al. |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0188943 A1 | 7/2017 | Braig et al. |
| 2017/0189625 A1 | 7/2017 | Cirillo et al. |
| 2017/0216524 A1 | 8/2017 | Haider et al. |
| 2017/0239415 A1 | 8/2017 | Hwang et al. |
| 2017/0258987 A1 | 9/2017 | Caspers |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0347971 A1 | 12/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Afonso |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0095052 A1 | 3/2019 | De et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0113515 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |
| 2022/0105270 A1 | 4/2022 | Doyle et al. |

FOREIGN PATENT DOCUMENTS

| | | |
|---|---|---|
| CA | 1040271 A | 10/1978 |
| CA | 3026851 A1 | 2/2020 |
| CN | 1297140 A | 5/2001 |
| CN | 101208699 A | 6/2008 |
| DE | 4200595 A1 | 9/1993 |
| DE | 19756872 A1 | 7/1999 |
| EP | 0026056 A1 | 4/1981 |
| EP | 0341049 A2 | 11/1989 |
| EP | 0496305 A2 | 7/1992 |
| EP | 0549341 S1 | 6/1993 |
| EP | 0867196 A2 | 9/1998 |
| EP | 0939451 A1 | 9/1999 |
| EP | 1376759 A2 | 4/2001 |
| EP | 1177802 B1 | 9/2004 |
| EP | 1491144 A1 | 12/2004 |
| EP | 1571582 A2 | 9/2005 |
| EP | 0801578 B1 | 7/2006 |
| EP | 2139382 A1 | 1/2010 |
| EP | 2397181 A1 | 12/2011 |
| EP | 2468338 A1 | 6/2012 |
| EP | 2666520 A1 | 11/2013 |
| EP | 2695573 A2 | 2/2014 |
| EP | 2703024 A1 | 3/2014 |
| EP | 2830499 A1 | 2/2015 |
| EP | 2897071 A1 | 7/2015 |
| EP | 2943149 A1 | 11/2015 |
| EP | 3177344 A1 | 6/2017 |
| EP | 3193979 A1 | 7/2017 |
| EP | 3314548 A1 | 5/2018 |
| EP | 3607985 A1 | 2/2020 |
| FR | 2096275 A5 | 2/1972 |
| GB | 1125897 A | 9/1968 |
| GB | 2443261 A | 4/2008 |
| JP | 51-125993 A | 11/1976 |
| JP | 02-131777 A | 5/1990 |
| JP | 2004-283378 A | 10/2004 |
| JP | 2005-326943 A | 11/2005 |
| JP | 2007-525276 A | 9/2007 |
| JP | 2008-513142 A | 5/2008 |
| JP | 2018-153569 A | 10/2008 |
| JP | 2012-527981 A | 11/2012 |
| JP | 2017-516548 A | 6/2017 |
| JP | 2017-525451 A | 9/2017 |
| JP | 2019-525276 A | 9/2019 |
| TW | 2004740148 A | 10/2007 |
| TW | M452390 U | 5/2013 |
| WO | 86/06796 A1 | 11/1986 |
| WO | 98/00193 A1 | 1/1998 |
| WO | 98/55073 A1 | 12/1998 |
| WO | 99/10040 A1 | 3/1999 |
| WO | 99/10049 A1 | 3/1999 |
| WO | 99/56803 A1 | 11/1999 |
| WO | 99/62576 A1 | 12/1999 |
| WO | 00/30705 A1 | 6/2000 |
| WO | 00/32258 A1 | 6/2000 |
| WO | 00/48112 A2 | 8/2000 |
| WO | 01/72354 A2 | 10/2001 |
| WO | 01/78812 A1 | 10/2001 |
| WO | 02/15954 A1 | 2/2002 |
| WO | 02/26282 A2 | 4/2002 |

(56) References Cited

FOREIGN PATENT DOCUMENTS

| | | |
|---|---|---|
| WO | 02/43866 A2 | 6/2002 |
| WO | 02/76535 A1 | 10/2002 |
| WO | 02/82990 A1 | 10/2002 |
| WO | 03/16882 A1 | 2/2003 |
| WO | 03/39362 A1 | 5/2003 |
| WO | 03/45233 A1 | 6/2003 |
| WO | 03/97133 A1 | 11/2003 |
| WO | 2004/043250 A1 | 5/2004 |
| WO | 2004/092715 A1 | 10/2004 |
| WO | 2005/051170 A2 | 8/2005 |
| WO | 2005/082436 A1 | 9/2005 |
| WO | 2005/110601 A1 | 11/2005 |
| WO | 2005/113036 A1 | 12/2005 |
| WO | 2006/053007 A2 | 12/2005 |
| WO | 2007/064385 A2 | 6/2007 |
| WO | 2007/066152 A2 | 6/2007 |
| WO | 2007/078937 A2 | 7/2007 |
| WO | 2008/024810 A2 | 2/2008 |
| WO | 2008/029403 A1 | 3/2008 |
| WO | WO 2008/048584 | 4/2008 |
| WO | 2008/133702 A1 | 11/2008 |
| WO | 2009/039203 A2 | 3/2009 |
| WO | 2009/045462 A1 | 4/2009 |
| WO | 2009/049252 A1 | 4/2009 |
| WO | 2009/066287 A2 | 5/2009 |
| WO | 2009/098648 A2 | 8/2009 |
| WO | 2009/134380 A2 | 11/2009 |
| WO | 2010/022069 A2 | 2/2010 |
| WO | 2010/053702 A1 | 5/2010 |
| WO | 2010/077279 A1 | 7/2010 |
| WO | 2010/132077 A1 | 11/2010 |
| WO | 2010/138848 A1 | 12/2010 |
| WO | 2010/139793 A1 | 12/2010 |
| WO | 2010/147659 A2 | 12/2010 |
| WO | 2011/031458 A1 | 3/2011 |
| WO | 2011/075042 A1 | 6/2011 |
| WO | 2011/095483 A1 | 8/2011 |
| WO | 2011/133823 A1 | 10/2011 |
| WO | 2012/045667 A2 | 4/2012 |
| WO | 2012/073032 A1 | 6/2012 |
| WO | 2012/108959 A1 | 8/2012 |
| WO | 2012/134588 A1 | 10/2012 |
| WO | 2012/177353 A1 | 12/2012 |
| WO | 2012/178134 A2 | 12/2012 |
| WO | 2013/050535 A2 | 4/2013 |
| WO | 2013/078200 A1 | 5/2013 |
| WO | WO 2013/097929 | 7/2013 |
| WO | 2013/134486 A2 | 9/2013 |
| WO | 2013/149186 A1 | 10/2013 |
| WO | 2013/177565 A1 | 11/2013 |
| WO | 2013/182321 A1 | 12/2013 |
| WO | 2014/029416 A1 | 2/2014 |
| WO | 2014/035672 A2 | 3/2014 |
| WO | 2014/109898 A1 | 7/2014 |
| WO | 2014/110538 A1 | 7/2014 |
| WO | 2014/149357 A1 | 9/2014 |
| WO | 2014/179774 A1 | 11/2014 |
| WO | 2014/194183 A2 | 12/2014 |
| WO | 2015/056259 A1 | 4/2015 |
| WO | 2015/061493 A1 | 4/2015 |
| WO | 2015/073211 A1 | 5/2015 |
| WO | 2015/081337 A2 | 6/2015 |
| WO | 2015/117082 A1 | 8/2015 |
| WO | 2015/117854 A1 | 8/2015 |
| WO | 2015/167201 A1 | 11/2015 |
| WO | 2015/177082 A1 | 11/2015 |
| WO | 2015/187366 A1 | 12/2015 |
| WO | 2016/004088 A1 | 1/2016 |
| WO | 2016/022650 A1 | 2/2016 |
| WO | 2016/041873 A1 | 3/2016 |
| WO | 2016/089702 A1 | 6/2016 |
| WO | 2016/141082 A1 | 9/2016 |
| WO | 2016/161254 A1 | 10/2016 |
| WO | 2017/004278 A1 | 1/2017 |
| WO | 2017/091624 A1 | 6/2017 |
| WO | 2017/105600 A1 | 6/2017 |
| WO | 2017/184988 A1 | 10/2017 |
| WO | 2017/187177 A1 | 11/2017 |
| WO | 2017/205816 A1 | 11/2017 |
| WO | 2018/009614 A1 | 1/2018 |
| WO | 2018/067748 A1 | 4/2018 |
| WO | 2018/120104 A1 | 7/2018 |
| WO | 2018/136799 A1 | 7/2018 |
| WO | 2018/204568 A1 | 11/2018 |
| WO | 2019/077482 A1 | 4/2019 |
| WO | 2019/094440 A1 | 5/2019 |
| WO | 2019/213493 A1 | 11/2019 |
| WO | 2019/246381 A1 | 12/2019 |
| WO | 2020/081393 A1 | 4/2020 |
| WO | 2021/011738 A1 | 1/2021 |

OTHER PUBLICATIONS

International Preliminary Report on Patentability in Application No. PCTUS/2017/012806, dated Jul. 26, 2018, 9 pages.
International Search Report and Written Opinion in Application No. PCTUS/2017/012806, dated Apr. 5, 2017, 14 pages.
Percival et al., "Closed-Loop Control and Advisory Mode Evaluation of an Artificial Pancreatic β Cell: Use of Proportional-Integral-Derivative Equivalent Model-Based Controllers," J Diabetes Sci Tech 2(4):636-644, Jul. 2008.

* cited by examiner

Insulin Delivery System

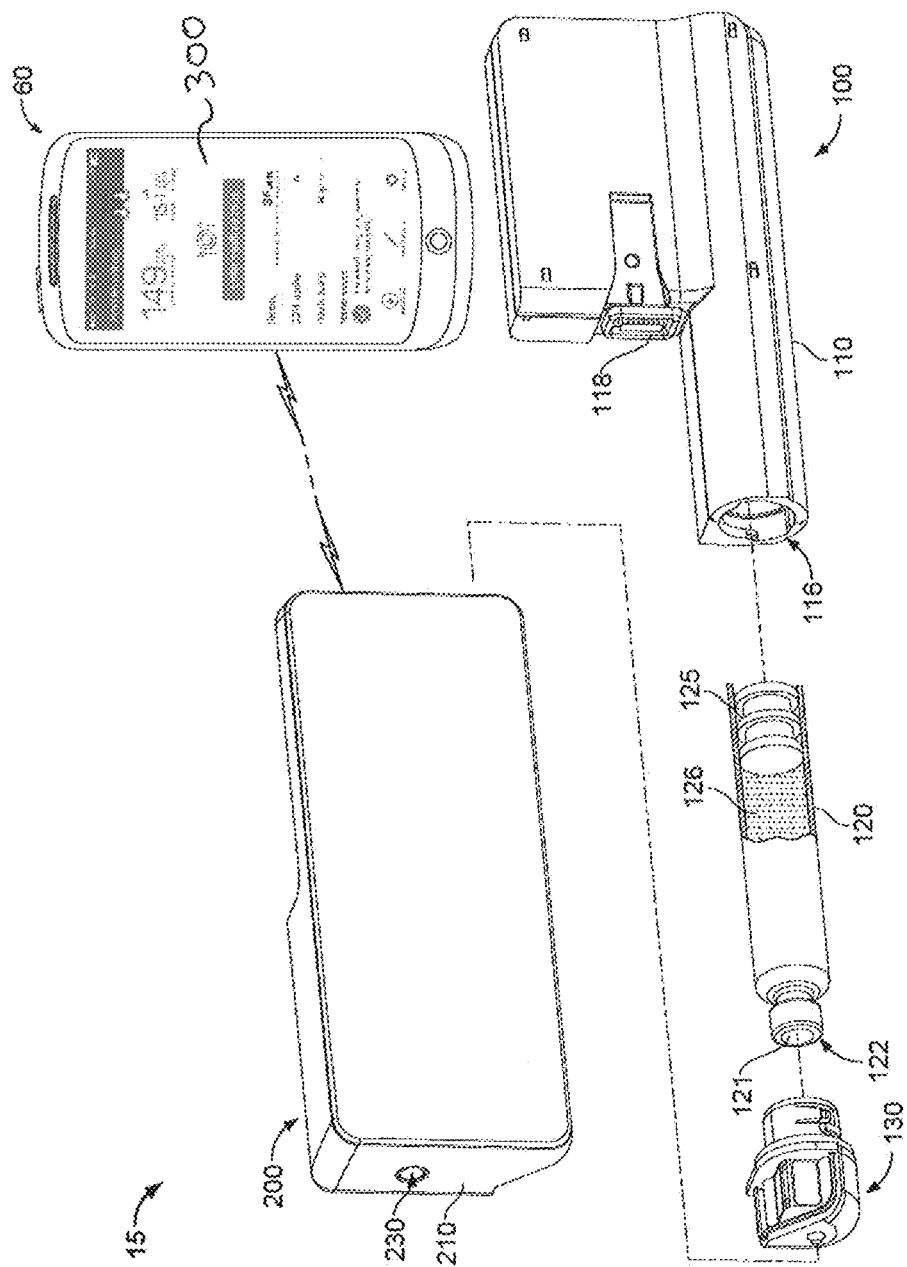
FIG. 1B Insulin Pump Details

Controller Details

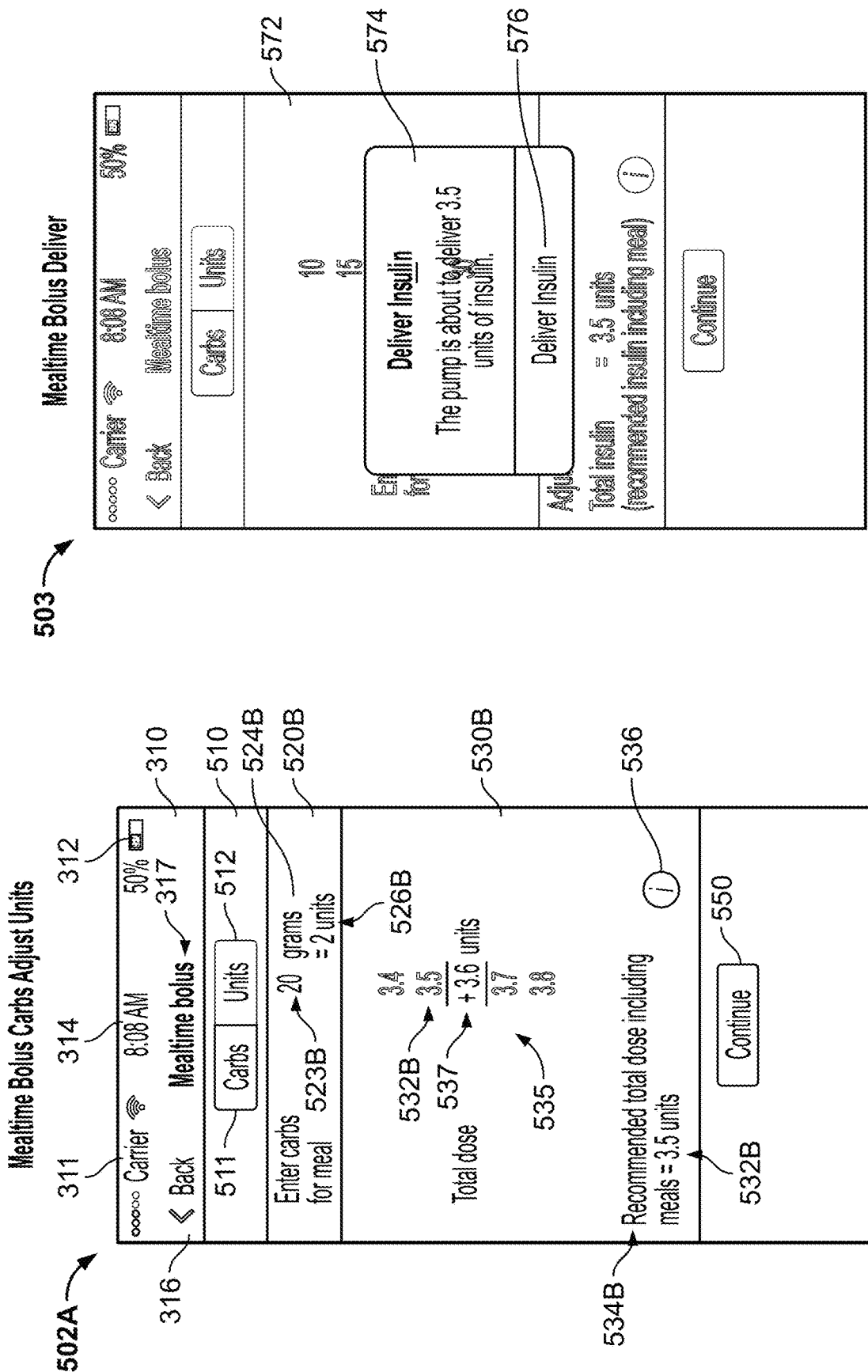

FIG. 4F

Bolus Information Box

537A

Carrier 🛜 8:08 AM 50% 🔋

< Back  Mealtime bolus

Recommended Total — 572

The recommended total dose is calculated using your Insulin to Carb Ratio of 1 unit to 10 grams of carbs and your CGM reading (3 min ago) 220 mg/dl — 538A

Adjust Total — 538B

You can manually adjust the total based on your situation. For example, you might reduce units if you are about to exercise hard or increase units if you have a cold. Talk to your doctor about how to make adjustments appropriate for you.

Insulin Delivered — 311 ooooo Carrier 🛜  6:48 PM  50% 🔋 — 312, 314

Sean Brewer — 315

🔁 — 313

INSULIN DELIVERED SUCCESSFULLY — 360

FIG. 7C — 703

Pump Maintenance Tubing Prime

PROTO.10  12:21  90%
Insulin Pump Maintenance — 310
[ Fill Cannula | Prime Tubing ]
Use this screen to prime tubing.
PLEASE ENSURE YOU ARE DISCONNECTED TO THE INSULIN PUMP BEFORE PROCEEDING.

Tubing Prime Options
4 Units — Contact Detach Prime
16 Units — XX Inch Tubing Prime
20 Units — XX Inch Tubing Prime

Pump Maintenance Confirmation

PROTO.10  12:20  90%
Insulin Pump Maintenance
[ Fill Cannula | Prime Tubing ] — 772
Use this screen to prime tubing.
PLEASE ENSURE YOU ARE DISCONNECTED TO THE...

Confirm Tubing Prime — 774
You are about to prime tubing with XX.XX units. Please ensure you are disconnected from the Bigfoot system.
[ Cancel | Deliver ]

4 Units
16 Units XX Inch...
20 Units XX Inch Tubing Prime

[ Continue ]

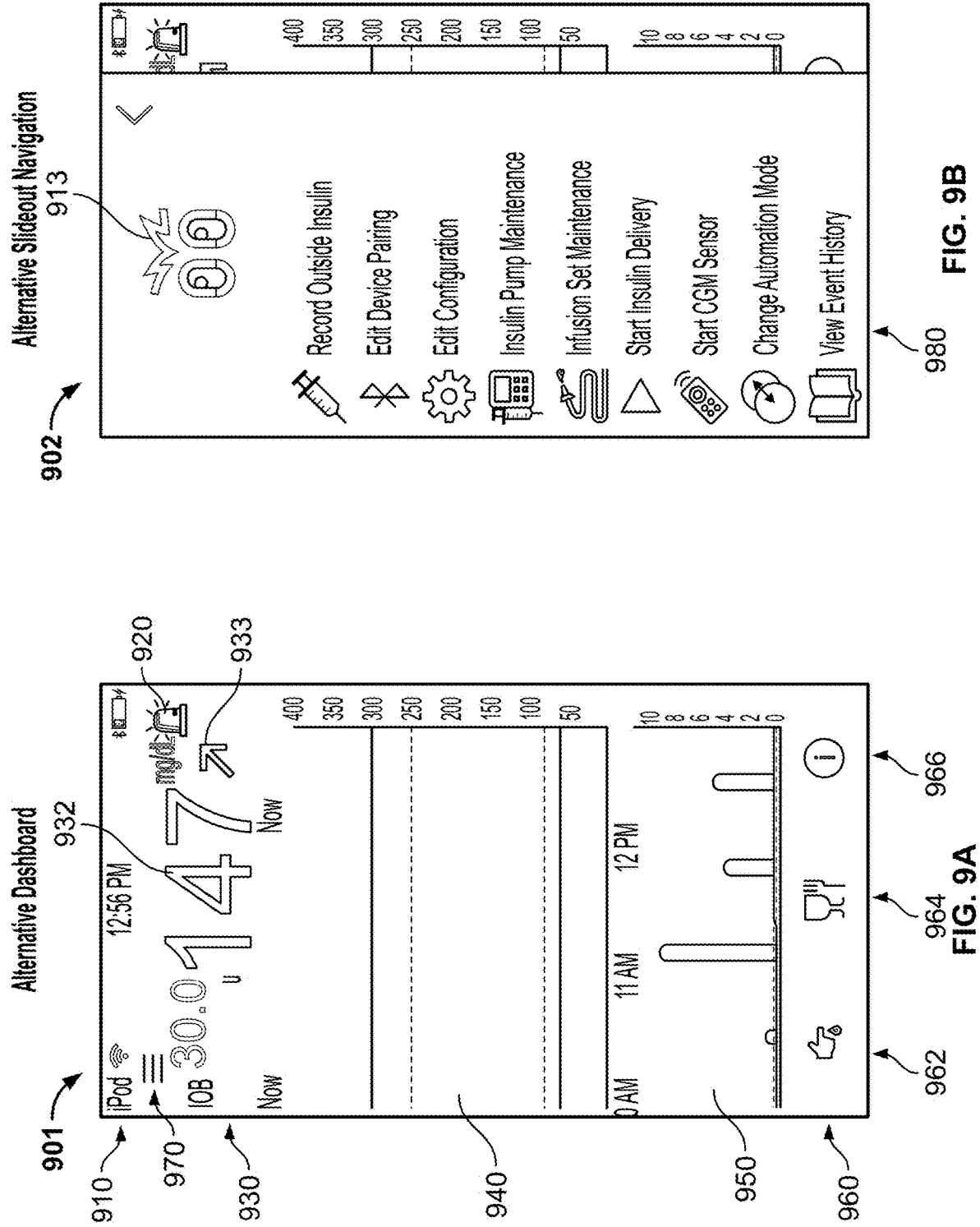

USER INTERFACE FOR DIABETES MANAGEMENT SYSTEM

CROSS-REFERENCE TO RELATED APPLICATIONS

This application is a continuation of U.S. application Ser. No. 15/402,493, filed Jan. 10, 2017, now U.S. Pat. No. 10,275,573, issued Apr. 30, 2019, which claims priority to U.S. Application Ser. No. 62/278,231, filed on Jan. 13, 2016.

TECHNICAL FIELD

This document relates a diabetes management system including a pump for dispensing a medicant and a control device for controlling the pump, the control device having a user interface for controlling functions of the pump and providing information related to operation of the pump and other information. For example, the control device can be a mobile computing device in wireless communication with one or more glucose sensors and/or insulin delivery devices and the user interface can be an application running on the mobile computing device.

BACKGROUND

Diabetes mellitus is a chronic metabolic disorder caused by an inability of a person's pancreas to produce sufficient amounts of the hormone, insulin, such that the person's metabolism is unable to provide for the proper absorption of sugar and starch. This failure leads to hyperglycemia, i.e., the presence of an excessive amount of analyte within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary that provides constant glycemic control in order to constantly maintain the level of blood analyte within normal limits. Such glycemic control is achieved by regularly supplying external drugs to the body of the patient to thereby reduce the elevated levels of blood analyte.

Conventionally, an external biologically effective drug (e.g., insulin or its analog) is commonly administered by means of multiple, daily injections of a mixture of rapid and intermediate acting drug via a hypodermic syringe. While this treatment does not require the frequent estimation of blood analyte, it has been found that the degree of glycemic control achievable in this way is suboptimal because the delivery is unlike physiological hormone production, according to which, hormones enter the bloodstream at a lower rate and over a more extended period of time.

Improved glycemic control may be achieved by the so-called intensive drug therapy which is based on multiple daily injections, including one or two injections per day of a long acting drug for providing a basal level of drug and additional injections of a rapidly acting drug before each meal in an amount proportional to the size of the meal. Although traditional syringes have at least partly been replaced by drug pens, the frequent injections are nevertheless very inconvenient for the patient, particularly those who are incapable of reliably self-administering injections.

Substantial improvements in diabetes therapy have been achieved by the development of other drug delivery devices, such as insulin pumps, relieving the patient of the need for syringes or drug pens and the administration of multiple, daily injections. Insulin pumps allow for the delivery of insulin in a manner that bears greater similarity to the naturally occurring physiological processes and can be controlled to follow standard or individually modified protocols to give the patient better glycemic control. In some circumstances, an insulin pump device can store (via input from a clinician or a user) a number of settings (e.g., dosage parameters or other settings) that are customized by the physician for the particular user. In one example, an infusion pump device can be programmed to store a user's insulin sensitivity (e.g., in units of mg/dL/insulin unit), which can be employed by the infusion pump system when calculating a correction bolus dosage for that particular user. In another example, an infusion pump device can be programmed to store a user's carbohydrate ratio (e.g., in units of g/insulin unit), which can be employed by the infusion pump system when calculating meal bolus dosage for that particular user. In many cases, these user-specific settings are manually input into the infusion pump device via user interface buttons on the infusion pump device. If any of these settings are erroneously input into the infusion pump system (e.g., due to a transcribing error or other error when manually inputting the data), the resulting consequences could lead to improper bolus dosage calculations resulting in blood glucose levels that are unnecessarily too high or too low.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Drug delivery devices have been utilized to assist in the management of diabetes by infusing drug or a suitable biologically effective material into the diabetic patient at a basal rate with additional drug or "bolus" to account for meals or high analyte values, levels, or concentrations. The drug delivery device typically is connected to an infuser, better known as an infusion set, by a flexible hose. The infuser typically has a subcutaneous cannula, and an adhesive backed mount on which the cannula is attached. The cannula may include a quick disconnect to allow the cannula and mount to remain in place on the skin surface of the user while the flexible tubing is disconnected from the infuser. Regardless of the type of drug delivery device, blood analyte monitoring is typically required to achieve acceptable glycemic control. For example, delivery of suitable amounts of drug by the drug delivery device requires that the patient frequently determine his or her blood analyte level and manually input this value into a user interface for the external drug delivery device, which then may calculate a suitable modification to the default or currently in-use drug delivery protocol, i.e., dosage and timing, and subsequently communicates with the drug delivery device to adjust its operation accordingly. The determination of blood analyte concentration is typically performed by means of an episodic measuring device such as a hand-held electronic meter, which receives blood samples via enzyme-based test strips and calculates the blood analyte value based on the enzymatic reaction. In recent years, continuous analyte monitoring has also been utilized with drug delivery devices to allow for greater control of the drug(s) being infused into the diabetic patients.

People with diabetes and their health care provider (HCP) bear a great deal of cognitive burden in managing intensive drug therapy. Delivering the correct amount of the drug at the correct time is an extremely challenging endeavor. It requires the patient to make dosing determinations multiple times per day and it requires a combination of the patient and the HCP to re-calibrate the therapeutic parameters of the therapy on an episodic time frame that varies from individual to individual.

In light of the many deficiencies and problems associated with current systems and methods for maintaining proper glycemic control, enormous resources have been put into finding better solutions. Developing workable solutions to the problem that are simple, safe, reliable and able to gain regulatory approval has, however, proved to be elusive. For years, researchers have contemplated coupling a continuous glucose monitoring system with an insulin delivery device to provide an "artificial pancreas" to assist people living with diabetes. Their efforts have yet to result in a commercial product. What has been needed is a system and method that provides a level of automatic control of drug delivery devices for improved drug delivery and glycemic control that is simple, safe, and reliable in a real world setting.

SUMMARY

User interfaces provided herein can simplify the management of diabetes, reduce the cognitive burden on users, and reassure the user that the diabetes management system is acting appropriately to manage the disease. User interfaces provided herein can be designed to highlight actionable information so that an ordinary user can quickly determine an appropriate corrective action. In some cases, user interfaces provided herein can be used to deliver mealtime boluses and/or input therapeutically relevant information. In some cases, user interfaces provided herein can display blood glucose data and project future blood glucose values. In some cases, user interfaces provided herein can display medication delivery information. In some cases, user interfaces provided herein can inform a user about upcoming predicted system maintenance activities and detected problems with the system that require maintenance.

In general, one innovative aspect of the subject matter described in this specification can be embodied in a medical infusion pump system that includes a portable housing defining a space to receive a supply of insulin; a pump drive system to dispense insulin from the portable housing when the supply of insulin is received in the space; control circuitry that electrically communicates with the pump drive system to control dispensation of the insulin from the portable housing when the supply of insulin is received in the space; a blood glucose detection device comprising at least one of a continuous glucose monitor or a blood glucose meter; a user interface device including a display screen and being configured to receive user input and present one or more outputs on the display screen based on information received from the blood glucose detection device. The user interface device is in communication with the control circuitry and provides a graphic user interface on the display screen that includes a first chart depicting a series of blood glucose values received from the blood glucose detection device aligned over a first axis to reflect the times that the blood glucose values were measured by the blood glucose detection device; and a second chart depicting a series of insulin bolus amounts administered by the pump drive system aligned over a second axis to reflect the times that the insulin bolus amounts were administered; wherein the first axis of the first chart and the second axis of the second chart are time-aligned.

These and other embodiments can each optionally include one or more of the following features. The user interface device can be a mobile computing device in wireless communication with the control circuitry. The mobile computing device can be in direct wireless communication with the blood glucose detection device. The mobile computing device can be in indirect wireless communication with the blood glucose detection device via the control circuitry. The medical infusion pump system can include a second blood glucose detection device; wherein the first blood glucose detection device comprises a continuous glucose monitor; wherein the second blood glucose detection device comprises a blood glucose meter; and wherein the first chart depicts a series of blood glucose values received from the continuous glucose monitor aligned over the first axis to reflect the times that the blood glucose values were measured by the continuous glucose monitor, and a series of blood glucose values received from the blood glucose meter aligned over the first axis to reflect the times that the blood glucose values were measured by the blood glucose meter.

The blood glucose values received from the continuous glucose monitor can be depicted using a first symbol and the blood glucose values received from the blood glucose meter can be depicted using a second symbol, the second symbol being larger than the first symbol. The graphic user interface can further include a current time line that passes through the first axis of the first chart and the second axis of the second chart to identify a current time with respect to the first and second charts; wherein the first chart further depicts a projection of future blood glucose values on a right side of the current time line. The graphic user interface can further includes a third chart depicting a step graph of a plurality of basal insulin delivery rates reflecting rates of basil insulin delivery by the pump drive system aligned over a third axis to reflect times of the basal insulin delivery rates; wherein the third axis of the third chart is time-aligned with the first axis of the first chart and the second axis of the second chart.

The graphic user interface can further include a current time line that passes through the first axis of the first chart, the second axis of the second chart, and the third axis of the third chart to identify a current time with respect to the first, second, and third charts; wherein the first chart further depicts a projection of future blood glucose values on a right side of the current time line; and wherein the third chart further depicts a projected basil insulin delivery rate on the right side of the current time line. The graphic user interface can further include a projected blood glucose value and a time for the projected blood glucose value, wherein the time for the projected blood glucose value is between 15 minutes and 4 hours after a most recent blood glucose measurement. The graphic user interface can further include an arrow indicating a projected profile of how blood glucose values are expected to change over a future time period, the time period being a length of time between 30 minutes and 4 hours.

In general, one innovative aspect of the subject matter described in this specification can be embodied in methods that include the actions of: receiving, at a mobile computing device, a plurality of blood glucose measurement values and corresponding measurement times for each of the blood glucose measurement values from a blood glucose detection device, the blood glucose detection device comprising at least one of a continuous glucose monitor or a blood glucose meter; receiving, at the mobile computing device, information indicating a plurality of insulin bolus dosage values for insulin bolus dosages administered by a pump device of the medical infusion pump system and corresponding bolus administration times for each of the insulin bolus dosage values; displaying, by the mobile computing device, a first graphic user interface having a first selectable input; receiving, by the mobile computing device, user selection of the first selectable input of the first graphic user interface; displaying, by the mobile computing device and in response to receiving the selection of the first selectable input, a second graphic user interface, the second graphic user interface including: a first chart depicting the plurality of blood glucose values received from the blood glucose detection device plotted over a first time axis according to the corresponding measurement times for each of the blood glucose measurement values; and a second chart depicting the plurality of insulin bolus dosage values for insulin bolus dosages administered by the pump device plotted over a second time axis according to the corresponding bolus administration times for each of the insulin bolus dosage values; wherein the first time axis of the first chart and the second time axis of the second chart are time-aligned.

These and other embodiments can each optionally include one or more of the following features. The mobile computing device can be in wireless communication with control circuitry in electrical communication with a pump drive system of the pump device to control dispensation of medicine from the pump device and wherein the bolus dosages administered by the pump device are administered in response to control signals communicated from the mobile computing device to the control circuitry. Receiving the plurality of blood glucose measurement values can include receiving a first plurality of blood glucose measurement values from a continuous glucose monitor and receiving a second plurality of blood glucose measurements from a blood glucose meter. The first chart can depict the first plurality of blood glucose measurement values received from the continuous glucose monitor aligned over the first time axis to reflect the times that each of the first plurality of blood glucose measurement values were measured by the continuous glucose monitor, and the second plurality of blood glucose measurement values received from the blood glucose meter aligned over the first time axis to reflect the times that each of the second plurality of blood glucose measurement values were measured by the blood glucose meter. The blood glucose measurement values received from the continuous glucose monitor can be depicted using a first symbol and the blood glucose measurement values received from the blood glucose meter are depicted using a second symbol, the second symbol being larger than the first symbol.

The second graphic user interface can further includes a current time line that passes through the first time axis of the first chart and the second time axis of the second chart to identify a current time with respect to the first and second charts; wherein the first chart further depicts a projection of future blood glucose values on a right side of the current time line. The second graphic user interface can further include a third chart depicting a step graph of a plurality of basal insulin delivery rates reflecting rates of basil insulin delivery by the pump device aligned over a third time axis to reflect times of the basal insulin delivery rates; wherein the third time axis of the third chart is time-aligned with the first time axis of the first chart and the second time axis of the second chart. The second graphic user interface can further include a current time line that passes through the first time axis of the first chart, the second time axis of the second chart, and the third time axis of the third chart to identify a current time with respect to the first, second, and third charts; wherein the first chart further depicts a projection of future blood glucose values on a right side of the current time line; and wherein the third chart further depicts a projected basil insulin delivery rate on the right side of the current time line.

The second graphic user interface can further include a projected blood glucose value and a time for the projected blood glucose value, wherein the time for the projected blood glucose value is between 15 minutes and 4 hours after a most recent blood glucose measurement. The second graphic user interface can further include an arrow indicating a projected profile of how blood glucose values are expected to change over a future time period, the time period being a length of time between 30 minutes and 4 hours.

The details of one or more implementations of the invention are set forth in the accompanying drawings and the description below. Other features, objects, and advantages of the invention will be apparent from the description and drawings, and from the claims.

BRIEF DESCRIPTION OF THE DRAWINGS

FIG. 1B depicts details of components of an exemplary insulin pump.

FIGS. 4A-4H illustrate various user interface screens of an example bolus calculator for a diabetes management system.

FIGS. 7A-7D illustrate example user interface screens for system maintenance.

FIG. 9A depicts an example alternative user interface dashboard.

FIG. 9B depicts an alternative example slide-out navigation screen.

Like reference symbols in the various drawings may indicate like elements.

DETAILED DESCRIPTION

Diabetes management systems provided herein can provide a user experience that reduces the cognitive burden on a person with diabetes (PWD) and their caregivers as they treat the disease. The user experience can be improved by providing a user interface that provides the user with actionable and easy to understand information. In some cases, the user interface can be provided on a mobile computing device (e.g., a smart phone or tablet device), which can be in wireless communication with an insulin pump, a continuous glucose monitor, a blood glucose monitor, and/or other components. Diabetes management systems and methods provided herein may be used and performed, respectively, by a user, for example, a type 1 or 2 diabetes patient or a caregiver of a diabetes patient. In some cases, the systems and methods may be adapted for use with additional chronic diseases or conditions, for example, unresponsive infections, cancer, cancer-related pain, chronic pain, gastrointestinal diseases or disorders, congestive heart failure, hemophilia, immune deficiencies, multiple sclerosis, and rheumatoid arthritis.

Diabetes Management System Overview

Figure 1A:
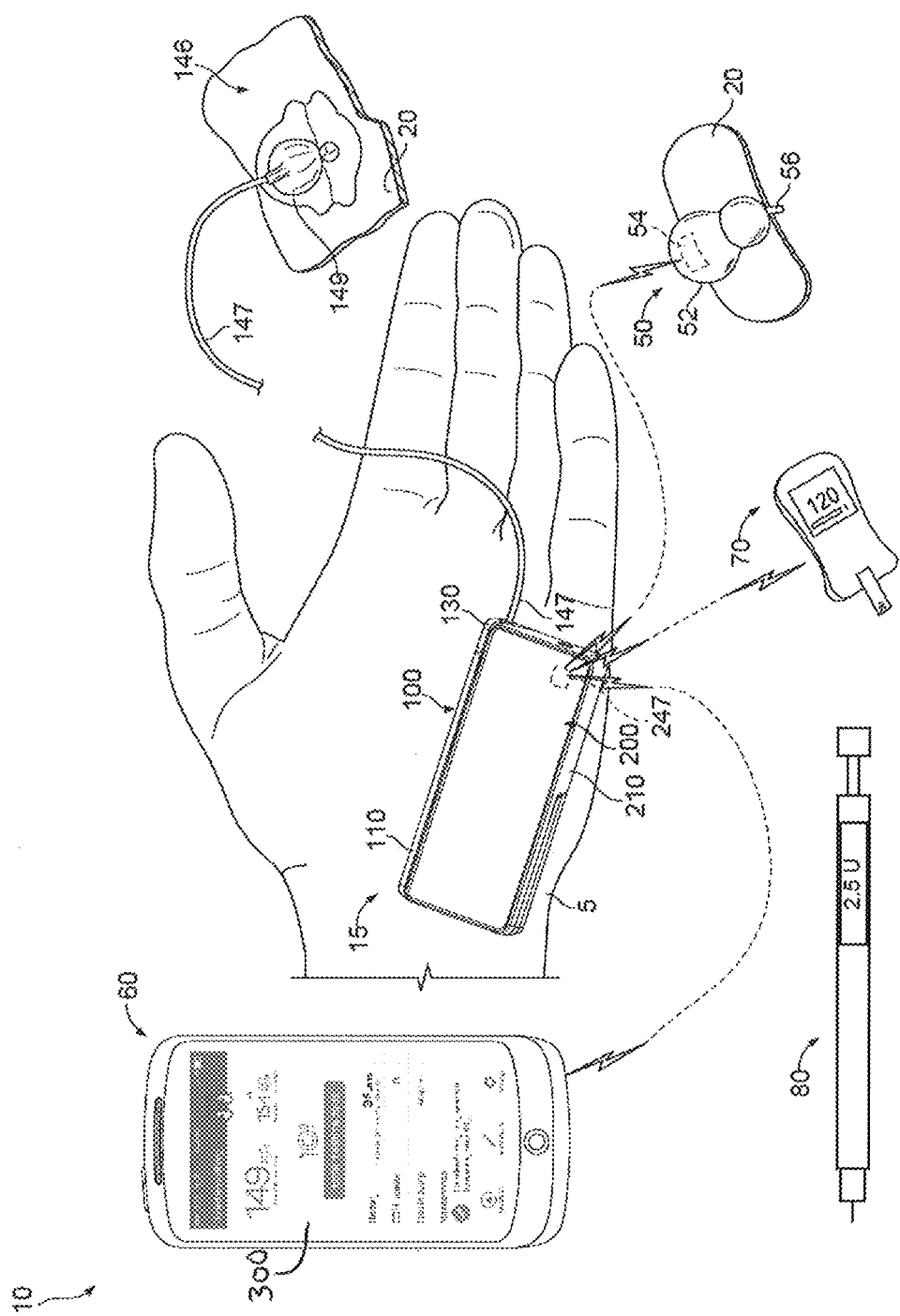
FIG. 1A is an exploded perspective view of an example diabetes management system.
Figure 1C:
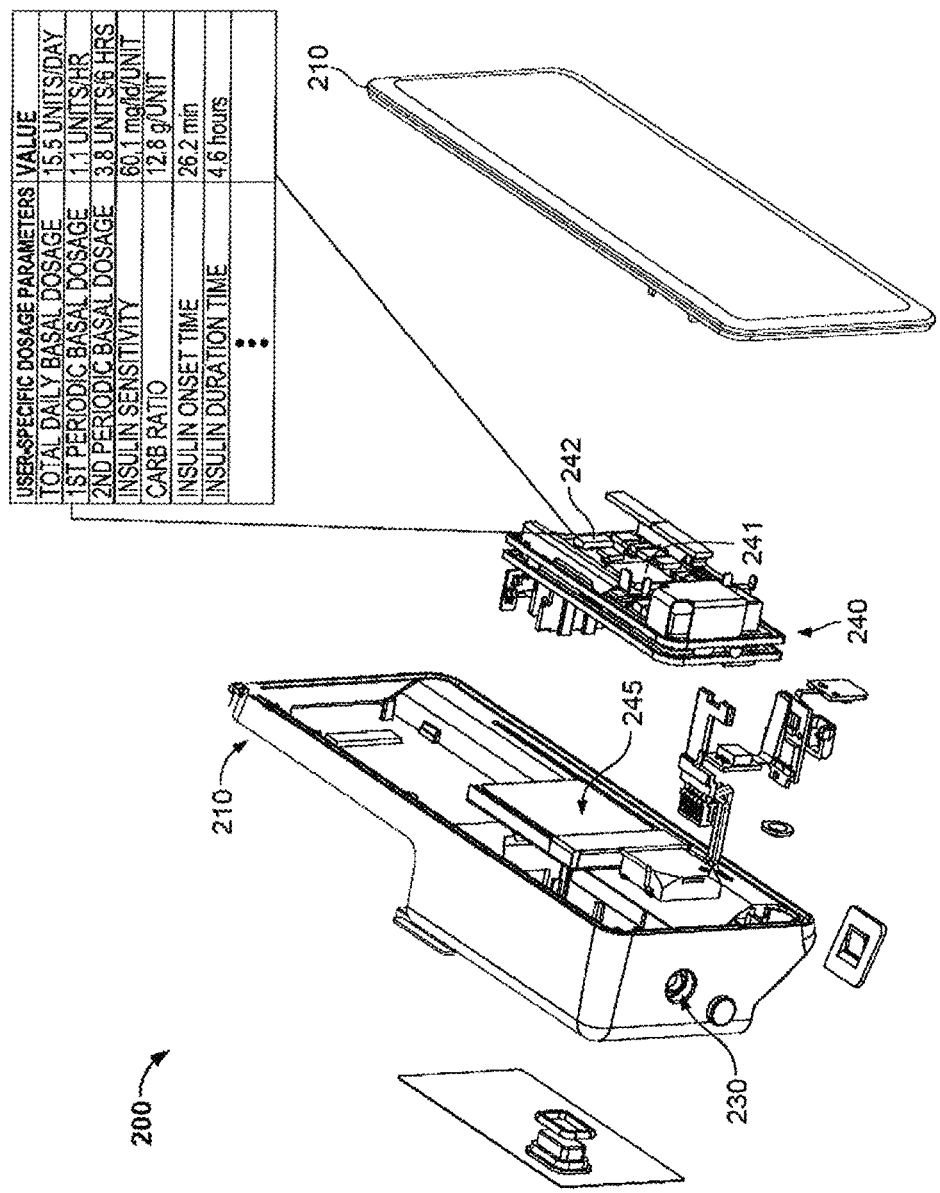
FIG. 1C depicts details of components of an exemplary insulin pump controller.

FIGS. 1A and 1B provide examples of a diabetes management system (DMS) 10 including an insulin pump assembly 15, a mobile computing device 60, a continuous glucose monitor 50, and a blood glucose monitor 70. FIG. 1C depicts the details of an exemplary pump controller, which can be used with DMS 10. Pump assembly 15 includes an infusion set 146 adapted to deliver insulin to an infusion set 146. In some cases, DMS 10 can include an insulin pen 80 or other insulin delivery device that can also be used to deliver insulin to a user. As shown, mobile computing device 60 is in wireless communication with insulin pump assembly 15. As shown, insulin pump assembly 15 is in wireless communication with continuous glucose monitor 50 and data from continuous glucose monitor 50 can be transferred to the mobile computing device 60 via insulin pump assembly 15. In some cases, continuous glucose monitor 50 can wirelessly communicate directly with mobile computing device 60. As shown, insulin pump assembly 15 is in wireless communication with blood glucose monitor 70 and data from blood glucose monitor 70 can be transferred to the mobile computing device 60 via insulin pump assembly 15. In some cases, blood glucose monitor 70 can wirelessly communicate directly with mobile computing device 60. In some cases, blood glucose monitor 70 can be unconnected from the insulin delivery system 10 and a user can manually input a blood glucose monitor reading into mobile computing device 60 (or into insulin pump assembly 15), either with or without a user prompt. In some cases, a blood glucose monitor 70 can be in wireless communication with continuous glucose monitor 50.

The features that are described herein can be extended to DMSs 10 that use alternative insulin delivery devices (e.g., insulin pens, patch pumps, syringes) and/or devices delivering other medicines (e.g., glucagon). In some cases, insulin pen 80 can be in wireless communication with mobile computing device 60. In some cases, user interfaces provided herein can be adapted to allow a user to manually input a bolus delivered using insulin pen 80. User interfaces described herein can also be used with any suitable insulin pump device, including patch pumps and/or other commercially available pumps. In some cases, an insulin pump assembly used in DMS 10 can have a unitary construction and have a reservoir adapted to be filled with insulin.

DMS 10 can be a closed-loop insulin delivery system that uses glucose data from continuous glucose monitor 50 and/or blood glucose monitor 70 in one or more feedback loops to change basal delivery rates, update parameters, settings, and/or models for dosage delivery that are specific to the user. In some cases, a pump controller (e.g., pump controller device 200) is part of pump assembly 15 and includes one or more processors adapted to alter basal delivery rates, change parameters, settings and/or models for dosage delivery based on glucose data from a continuous glucose monitor 50 and/or a blood glucose meter 70. In some cases, algorithms for changing basal delivery rates, update parameters, settings, and/or models for dosage delivery that are specific to the user can be present on mobile computing device 60 and/or on a remote server that is accessed by the mobile computing device 60 via the cloud.

Mobile computing device 60 can serve as the user interface of DMS 10. As shown, mobile computing device displays user interface home screen 300, which can allow a user to see actionable data and send commands to pump assembly 15. In some cases, user interfaces provided herein are all present on mobile computing device 60 and are not present on a pump assembly 15, which can eliminate a need for a dedicated display and user input device on pump assembly 15, reducing costs and energy expenditure for pump assembly 15. In some cases, pump assembly 15 can include between zero and five LED indicators adapted to light to inform the user of certain conditions. In some cases, pump assembly 15 lacks a graphical display. In some cases, pump assembly 15 can provide audible, visual, and/or tactile (vibration) alarms to alert a user to a need to access mobile computing device 60 to monitor DMS 10. In some cases, pump assembly 15 lacks any user selectable buttons or icons, but can optionally use an accelerometer to detect motion of the pump assembly 15 for receiving user inputs to the pump assembly 15. In some cases, pump assembly 15 includes between zero and two user actionable buttons or icons. By placing most or all of the user interface on mobile computing device 60 (e.g., a smart phone or tablet device), a user can avoid attracting unwanted attention when inputting data into the DMS. Moreover, smart phones typically have more robust graphical displays, which can improve the user experience as compared to the types of displays typically added to insulin pump devices. In some cases, however, user interfaces provided herein can be present on pump assembly 15, on a web portal, on a continuous glucose monitor controller, on blood glucose meter 70, or another part of a DMS system.

User Interface

Figure 2:
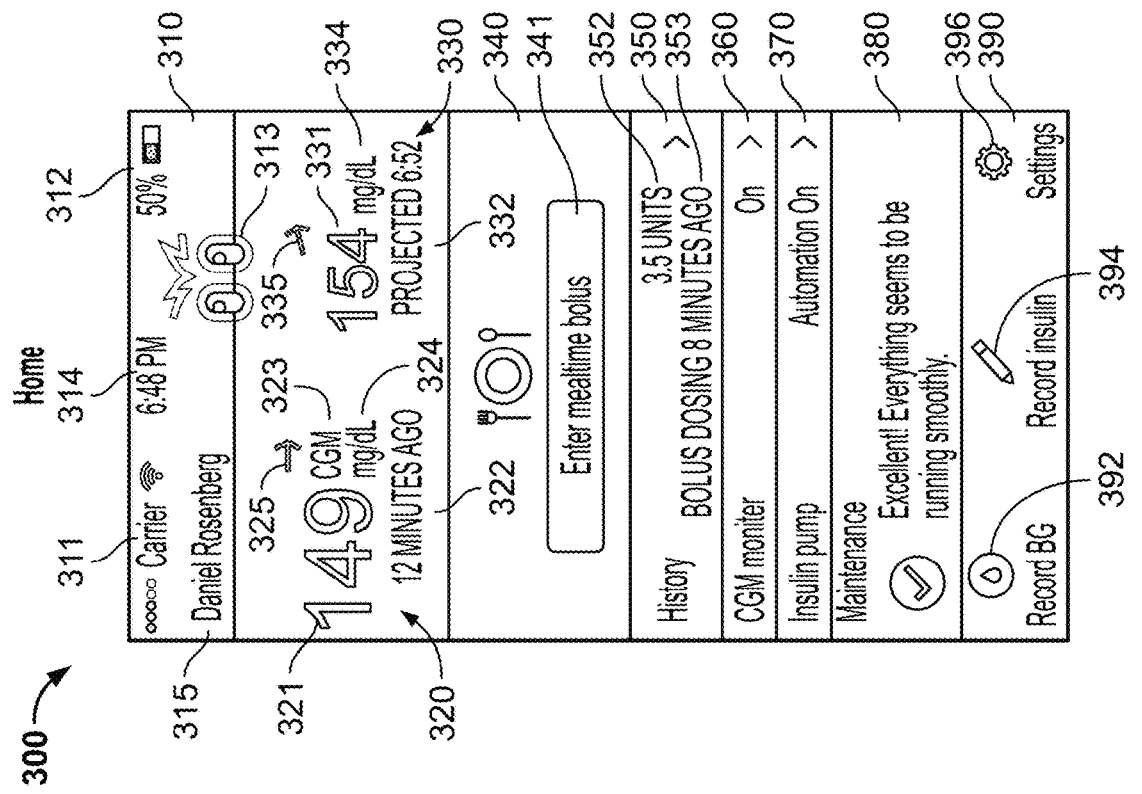
FIG. 2 is an example home screen of a mobile computing application for a diabetes management system.

FIG. 2 depicts an exemplary home screen 300 for DMS 10, which can appear on a mobile computing device 60 when a user selects an icon for the DMS application. If the user is already logged in, home screen 300 can pop up whenever the user selects an icon for the DMS control application. If the user is not logged in, a log-in screen can appear for the user to enter secure identifying information (e.g., a user name and password, a thumb print, an iris scan, etc.). Moreover, as discussed below, the DMS control application can also prompt a user to pair one or more insulin delivery devices, continuous glucose monitors, and/or blood glucose monitors during an initial log in and/or if mobile computing device 60 fails to find a paired insulin delivery device, continuous glucose monitors, and/or blood glucose monitors.

Home screen 300 can provide the user with a simplified view of the DMS status to help the user quickly understand whether the DMS system is operating appropriately and promote routine activities, while also allowing the user to access additional data if the user is interested in more detailed system information. As shown, home screen 300 includes a header 310, which can include mobile and Wi-Fi signal strength indicators 311, a mobile computing device power display 312, a logo 313, a time display 314, and a user name 315. Header 310 can provide the user with comfort about the system status of the mobile computing device 60 and assure the user that the mobile computing device 60 is their personal mobile computing device 60.

Home screen 300 includes a most recent glucose measurement field 320 that includes a most recent glucose measurement 321 which can be displayed as the most prominent number, along with a time display 322 of the timing of glucose measurement field 320, an identification of the glucose measurement device 323, and the units 324 for glucose measurement 321. In some cases, the most recent glucose measurement 321 can be from a continuous glucose monitor (CGM). In some cases, the most recent glucose measurement 321 can be from a blood glucose meter (BGM). In some cases, the most recent glucose measurement 321 will always display the most recent glucose measurement regardless of the measurement device. Glucose measurement 321 can be the most prominent number because it is typically the number that a person with diabetes (PWD) or a caregiver is most concerned about monitoring to ensure the diabetes is being treated appropriately. Accordingly, a very prominent display of the most recent blood glucose measurement 321 can help assure a user that the DMS is acting appropriately. In some cases, the most recent glucose measurement field 320 can include a trend arrow 325, which can indicate the slope of the recent blood glucose measurements from a continuous glucose monitor.

Home screen 300 can, in some cases, also include a projected condition display 330 indicating how glucose levels are expected to change going forward, which is distinct from the typical display of blood glucose trend indicators, such as trend arrow 325. As shown, home screen 300 displays a numerical projected glucose level 331 along with a future time 332 for which that glucose value is projected and the units 334. In some cases, future time 332 for projected glucose value 331 is between 15 minutes and two hours in advance of the time of the most recent blood glucose value 320. In some cases, future time 332 is between 30 minutes and 1 hour in advance of the time of most recent blood glucose value 320.

Figure 8:
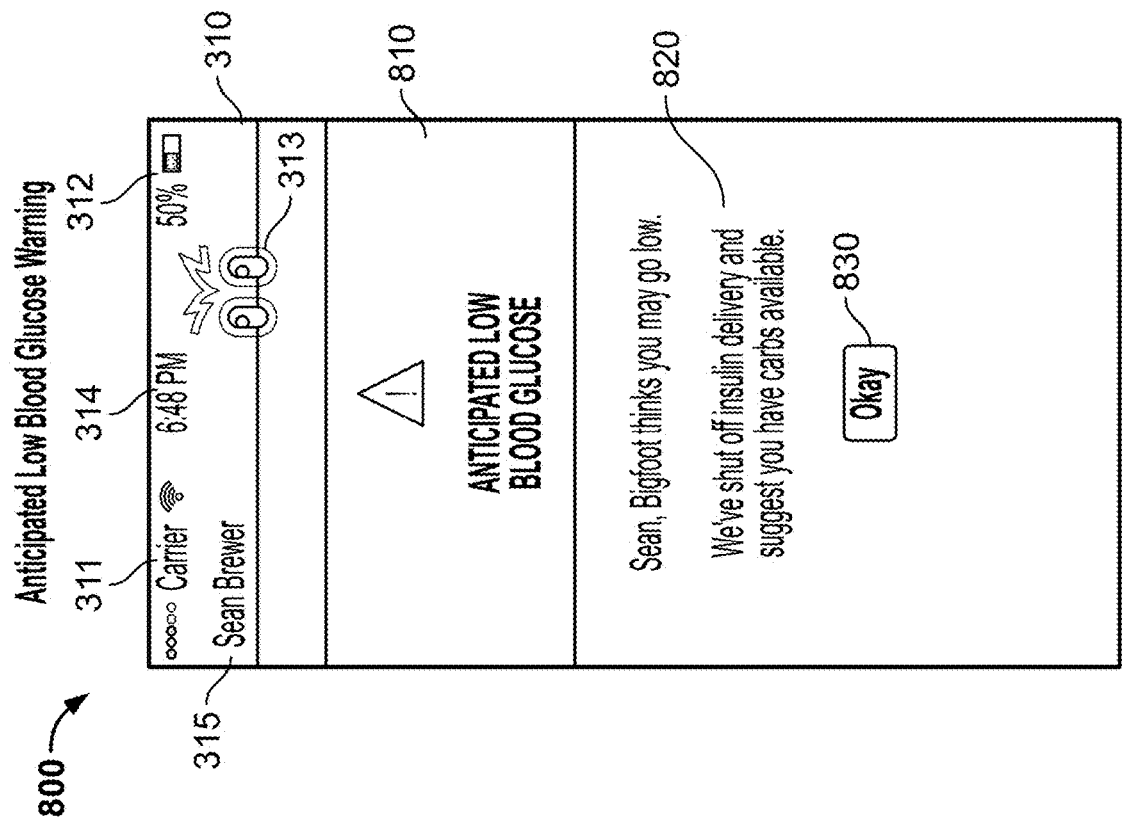
FIG. 8 depicts an example user interface alarm screen.

In some cases, projected condition display 330 can include a prediction arrow 335 that can indicate the direction and/or rate of projected change. As shown, prediction arrow 335 can have a different slope than trend arrow 325, which is because the trend arrow is based on a plot of past glucose data alone. In some cases, prediction arrow 335 is depicted with projected glucose value 331. In some cases, prediction arrow 335 can be present without a projected glucose value 331. In some cases, prediction arrow 335 can be straight to indicate that the glucose values are projected to steadily increase, decrease, or remain relatively static over the next one, two, three, or four hours. In some cases, a slope of prediction arrow 335 can indicate the approximate expected rate of change. In contrast to trend arrow 325, prediction arrow 335 can display the trajectory of projected glucose values, not just the trajectory of previously recorded glucose values. In some cases, prediction arrow 335 can be curved to indicate that projected glucose levels are expected to rise then fall (e.g., after a meal and bolus) or fall then rise (e.g., after the system has detected a projected low and reduced basal delivery rates). In some cases, projected condition display 330 can include a text string with or without prediction arrow 335 and/or projected glucose value 331 to indicate how the DMS 10 expects glucose values to change over the next 15 minutes to 4 hours. Exemplary text strings could include the following: "Glucose values expected to remain with 20 mg/dL of target over the next two hours"; "Glucose values expected to rise over the next hour, but return within 20 mg/dL of target within three hours"; "Glucose values expected to fall over the next 30 minutes to be within 20 mg/dL of target"; "Glucose values projected to continue to rise, DMS recommends a correction bolus"; and "Glucose values projected to fall quickly, DMS recommends that you eat sugar or inject glucagon." In the case that the DMS projects a high or low that cannot be corrected with an adjustment to a basal rate using a closed loop algorithm, the DMS system can provide an alarm (for example, on the mobile computing device 60, pump assembly 15, or a combination thereof) to get the user's attention, thus the typical display of projected glucose values should reassure the user that the DMS 10 is acting appropriately to manage the PWD's diabetes. For example, the DMS 10 can perform an analysis to determine if a projected high or low BGL can be corrected with an adjustment to a basal rate. If the DMS 10 determines that the BGL cannot be corrected with an adjustment to the basal rate, the DMS 10 provides an audio, visual, and/or tactile alarm to alert the user to the projected high or low. An example alarm is depicted in FIG. 8, discussed below. An advantage of a projected glucose value 331, a prediction arrow 335 depicting how glucose values are expected to change, and/or a text string explaining how glucose values are expected to change over the next few hours is that the user does not need to conduct a self-evaluation that considers trends in the glucose data, amounts of food consumed, and amounts of recently insulin delivered to evaluate whether the DMS is operating appropriately.

In some commercial devices, an amount of insulin on board (IOB) is calculated to tell a user an estimate of how much insulin has been delivered but not yet acted, which some diabetics use to adjust treatment. In some cases, home screen 300 can display an indication of an amount of insulin on board (IOB) in order to reassure users that are accustomed to seeing an IOB. In some cases, home screen 300 can eliminate an IOB display due to the presence of a projected glucose value, a projected glucose trajectory, or a textual string. In some cases, a user can set an option regarding whether to see an IOB value on home screen 300. For example, a setup screen can provide a control that allows the user to elect to display an IOB value on the home screen or on another screen.

Referring back to FIG. 2, home screen 300 includes a history field 350 configured to indicate to the user the most recent relevant event, which can typically be a bolus amount 352 along with the timing 353 of the bolus. History field 350 can ensure that a user can quickly confirm that a recent bolus (e.g., for a recent meal) was delivered. Bolus history field 350 is a more intuitive way for a user, especially users new to the management of diabetes, to understand the currently enacted treatment. If a user clicks on history field 350, a history user interface can appear, such as those discussed below in relationship to FIGS. 3A and 3B.

History User Interfaces

Figure 3B:
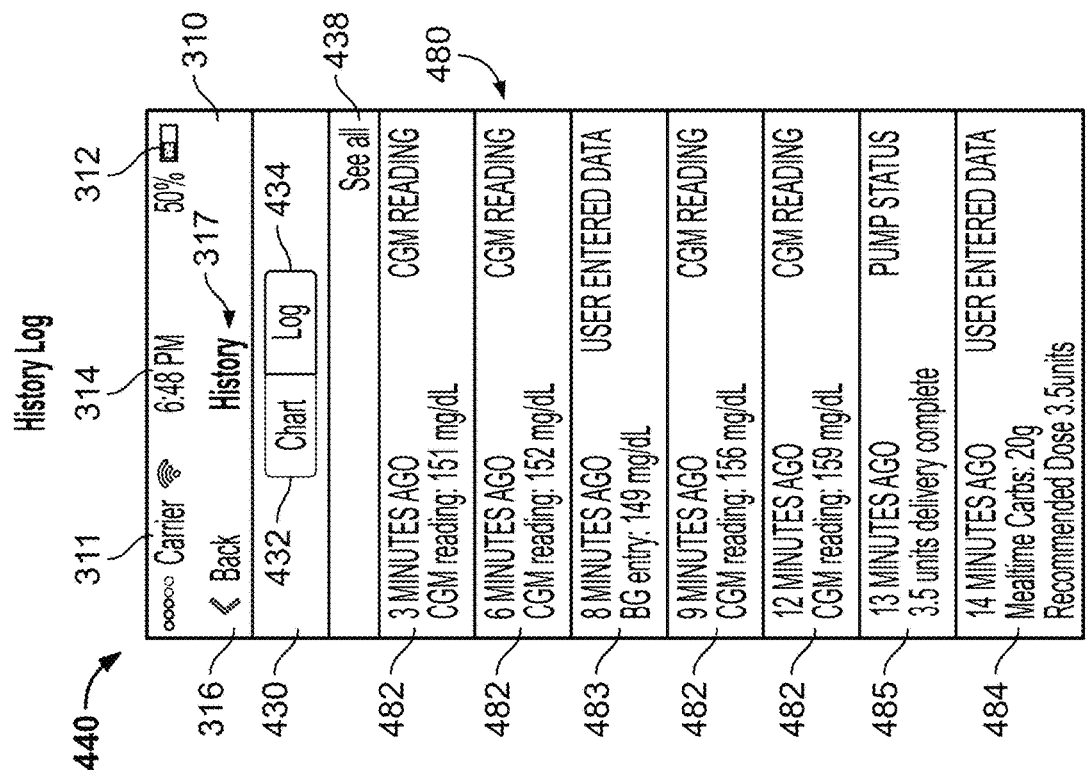
FIG. 3B is an example history log for a diabetes management system.
Figure 3A:
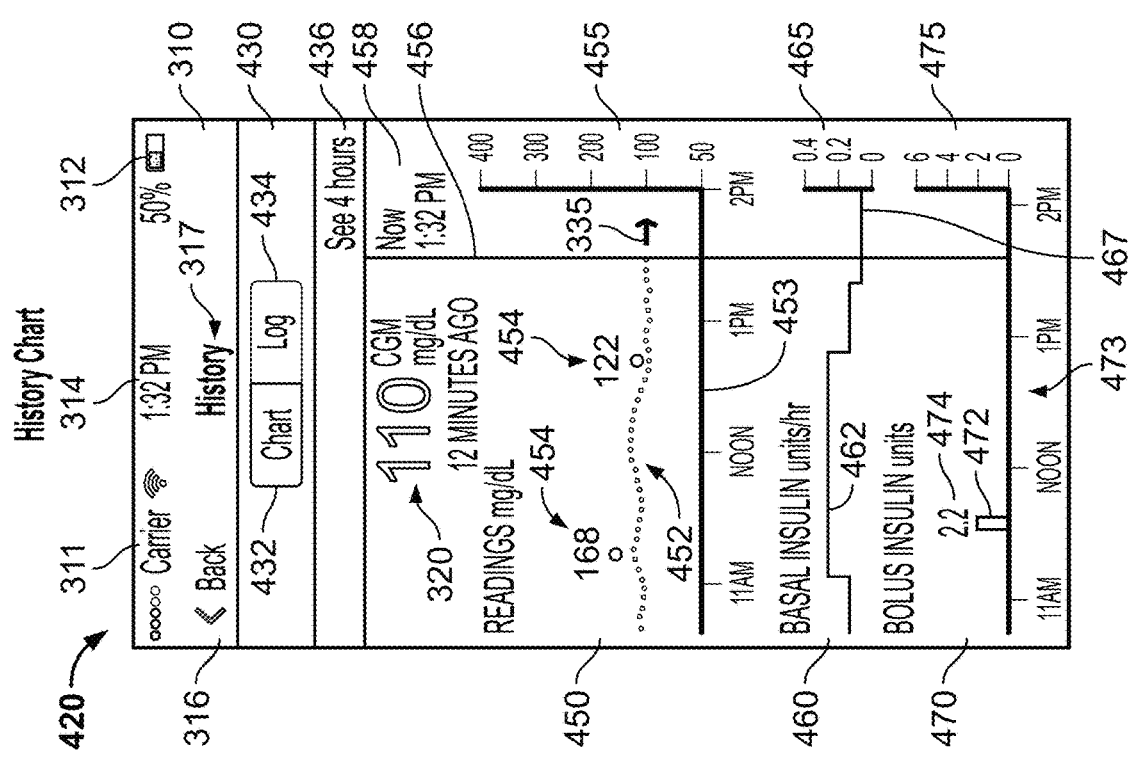
FIG. 3A is an example history chart for a diabetes management system.

When a user clicks on the history field 350 on home screen 300, the user can arrive at one of the history screens 420 or 440 depicted in FIGS. 3A and 3B. As shown, screens 420 and 440 both include headers 310 similar to the header on home screen 300, but having a title 317 and a back button 316. Back button 316 can bring the user back to home screen 300. A toggle field 430, below header 310, allows a user to toggle between history screens 420 and 440 by clicking on chart control 432 for history chart screen 420 and by clicking on log control 434 for history log screen 440.

History chart screen 420 provides time-aligned graphical charts 450, 460, and 470. Glucose value chart 450 shows both continuous glucose monitor glucose values 452 and blood glucose meter glucose values 454 plotted along a time x-axis 453 and a glucose value y-axis 455. As shown, blood glucose meter and continuous glucose meter values are visually distinct (e.g., different color, different size, etc.). In some cases, data 454 from a blood glucose meter is more prominent because blood glucose meter data is more accurate and less frequent. In some cases, data 454 from a blood glucose meter can display the numerical value of the reading to make it clear that the data point is more accurate. A current time indicator line 456 extends down the screen and a time indicator 458 indicates the current time. The data to the left of time indicator line 456 is historical data, while the data to the right of the indicator line 456 can be blank, can project one or more predicted glucose values (for example, in a different color or using a different dash pattern), or can project a range of possible glucose values. As shown, the data to the right of indicator line 456 can include prediction arrow 335 having a shape and/or slope as discussed above. In some cases, projected glucose values can appear like a shaded triangle to indicate a range of possibilities. Beneath glucose value chart 450, charts 460 and 470 depict the basal delivery rates 462 over time and a history of bolus deliveries over time, respectively. Basal dosage chart 460 indicates the basal delivery rates, which DMS 10 automatically adjusts based on data from a continuous glucose monitor, blood glucose meter, and/or recent insulin deliveries. The y-axis 465 of basal dosage chart 460 includes basal delivery rates per hour. On the right side of time indicator 456 basal dosage chart can be blank or display the currently scheduled basal delivery rate 467. Although actual basal insulin may be delivered as discrete units at regular or irregular intervals based on the specifics of the insulin pump, chart 460 depicts the basal delivery as a step graph 462 showing a continuous insulin delivery as a rate over time. Bolus dosage chart 470 depicts a history of larger dosages of insulin 472 along the time x-axis 473 as bars 472 on a graph with units of insulin along the y-axis 475. Each bar can include a numerical display 474 of units delivered. In some cases, charts 460 and 470 are separate due to the different y-axis units. In some cases, charts 460 and 470 can overlie each other and each bolus bar labeled to indicate the amount of the bolus, such as depicted in the alternative user interface depicted in FIG. 9A. The history screen 420 can typically display 4 hours of data, but a user can click on 436 to change the amount of time displayed.

History log screen 440 can provide a log 480 of all glucose readings 482 and 483 (both from a continuous glucose monitor and a blood glucose meter, respectively) and insulin delivery tasks 484 and 485 (e.g., bolus deliveries and/or changes to basal insulin rates) as separate entries, each with a time, a label, and a summary. A filter 438 can be used to select the types of data displayed in log 480.

After a user has gained confidence in the DMS, a user might not typically access history screens 420 and 440. Nonetheless, the presence of history screens 420 and 440 can allow a user to gain trust in the DMS by allowing the user to see all activates. Moreover, users might access history screens 420 and 440 if the user believes that the system is acting unusually. Additionally, clinicians and other care providers can use history screens to monitor the DMS to determine if the DMS is acting appropriately.

Bolus Entry

Referring back to FIG. 2, in some cases home screen 300 also prominently displays a bolus entry user actionable display 340, including an icon 341 that allows a user to enter carbohydrates and/or units of insulin to properly dose insulin in response to a meal. The button for bolus entry user actionable display 340 is prominently displayed because it is expected to be the most common action of a user using a closed-loop diabetes management system. For example, the button for bolus entry can be displayed as larger than any other single control on the home screen 300. Home screen 300 can additionally include additional user selectable icons that allow the user to provide additional data to DMS 10, but less routine tasks (e.g., recording outside insulin) can be deemphasized as compared to more routine tasks (e.g., inputting a mealtime bolus). As shown in FIG. 2, navigation row 390 can include additional user selectable icons.

Figure 4B:
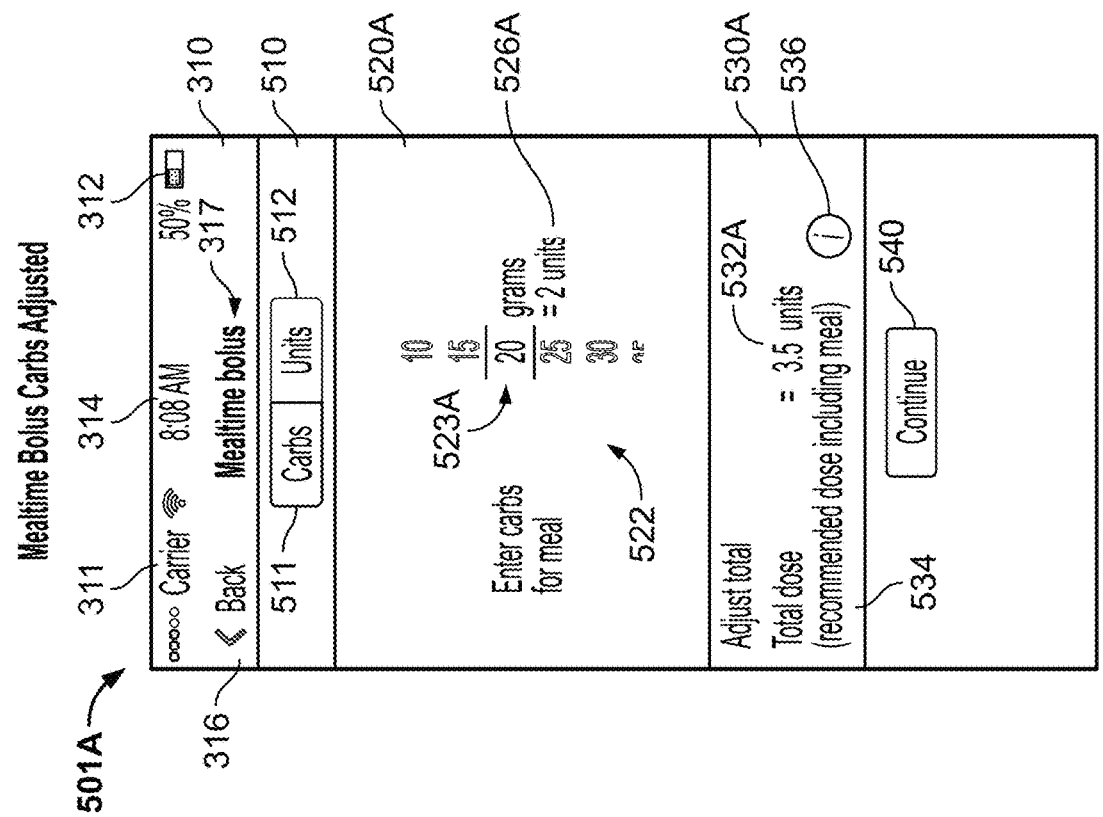
Figure 4A:
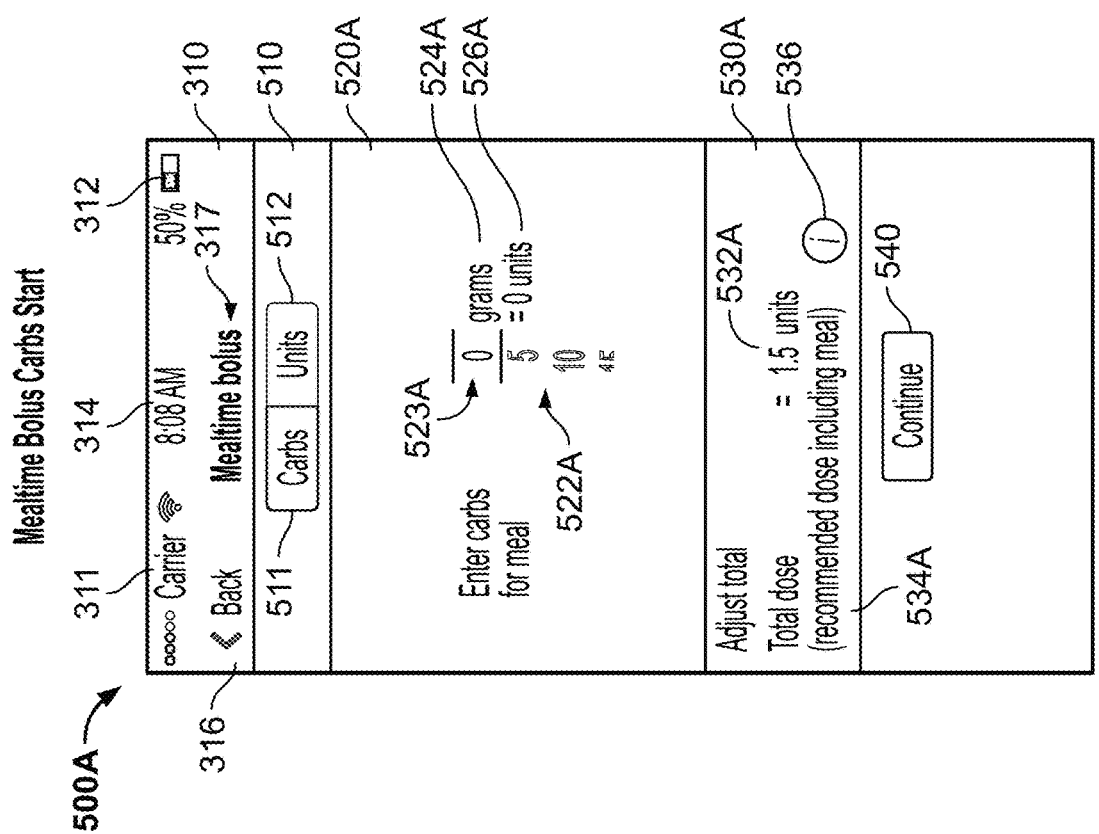

When a user selects the bolus entry user actionable display 340 or icon 341, a user can be delivered to a bolus calculator screen, such as screen 500A as depicted in FIG. 4A. The bolus calculator thus minimizes the amount of information that the user must comprehend when considering a mealtime bolus. FIGS. 4A-4G depict how a bolus calculator can be used. Again, the bolus calculator screens include a header 310 that can include a title 317 and a back button 316, which can be clicked to return to home screen 300. Beneath header 310, a toggle field 510 allows a user to switch between entering carbs consumed and units of insulin by selecting carbs control 511 or units control 512. As shown in FIG. 4A, the carbs control 511 is selected. If the units control is selected, the user will be delivered to screen 500C as depicted in FIG. 4G. The toggle between carbs and units of insulin allows for different users to use the bolus calculator, as some users may think about meals in terms of the number of carbohydrates consumed while others think about meals in terms of units of insulin needed for the meal.

In screen 500A, a user first scrolls down to a number of carbs 523A using scroll wheel 522A to estimate a number of carbs for the meal, changing the screen to appear similar to screen 501A depicted in FIG. 4B. The units 524A for the scroll wheel 522A are clearly displayed to avoid user confusion about the data being entered. As the grams of carbs 523A is adjusted using scroll wheel 522A, the user interface dynamically updates a conversion of the carbs 523A to units of insulin 526A for the user, which can be based on the user's carbohydrate to insulin ratio. Screens 500A and 501A further depict a total dose field 530A that includes an adjusted total dose 532A of insulin delivery that displays a calculated correction of the dose. Text string 534A can indicate that the DMS recommends the calculated correction of the dose. An information button 536 can be clicked on to explain to a user how this is calculated. An example of the information that can be included on the screen when clicking information button 536 is shown in screen 537A in FIG. 4F, discussed below. When the user first arrives at the bolus calculator screen and the carbs scroll wheel 522A initially has the selected value of carbs 523A set to zero, the total dose 532A will indicate the amount of the adjustment, so a user can see how much of an adjustment the DMS is making. This adjustment can be based on factors such as the amount of insulin on board, current glucose values and/or trends, and/or additional information about the user.

Once the user has entered the number of carbs (which can be left at zero), the user can select continue button 540 to go to screen 502A as depicted in FIG. 4C. In some cases, the text of continue button 540 can instead recite "Adjust Insulin." After selecting continue button 540, the fields 520A and 530A change to fields 520B and 530B as shown in FIG. 4C. In field 520B, the user selected number of carbs 523A is displayed as the selected number of carbs 523B without any scroll wheel to indicate that this value is set. Field 520B also displays the units 524B and the conversion to units of insulin 526B so that the user can remember the amount of units being delivered due to the consumption of food. If the user wishes to change the number of carbs entered, the user can click on field 520B to have the screen revert to screen 501A. Field 530B then allows the user to make a personal adjustment using a scrolling wheel 535 to the total dose. The recommended total dose 532A from screen 501A can appear at the bottom of field 530B and/or have a distinct appearance in the scrolling wheel 535 to remind a user what the DMS has calculated for the total dose. Screen 502A allows the user to adjust the number of units so that the user has ultimate control over the bolus amount. For example, a user may want to adjust the bolus amount from the DMS calculated amount if the user is feeling sick or if the user is about to exercise. Being able to adjust the number of units for the total dose 537 can be useful when a user is building trust in the system. Once the user has selected the total dose 537 on scrolling wheel 535, the user can hit continue button 550 to bring up screen 503. In screen 503, depicted in FIG. 4D, a confirmation box 574 pops up to inform the user that the pump is about to deliver a certain number of units of insulin to the user and has the user click on selectable button 576 to deliver the insulin. The display of box 574 results in the reminder of the screen being shaded 572. FIG. 4E depicts a screen 504 indicating an announcement that insulin has been delivered successfully. In some cases, a screen can appear showing the progress of the bolus. For example, a user interface can show a progress bar.

FIG. 4F displays a bolus information box that can be displayed when a user selections information icon 336 in any of FIGS. 4A-4C, 4G, and 4F. Screen 537 explains how the recommended dose is based on an insulin to carb ratio and blood glucose readings 538A and explain that a user can manually adjust the total 538B. The box can be over a shaded background 572. A user can select an "OK" button 539 to exit the information box.

Figure 4H:
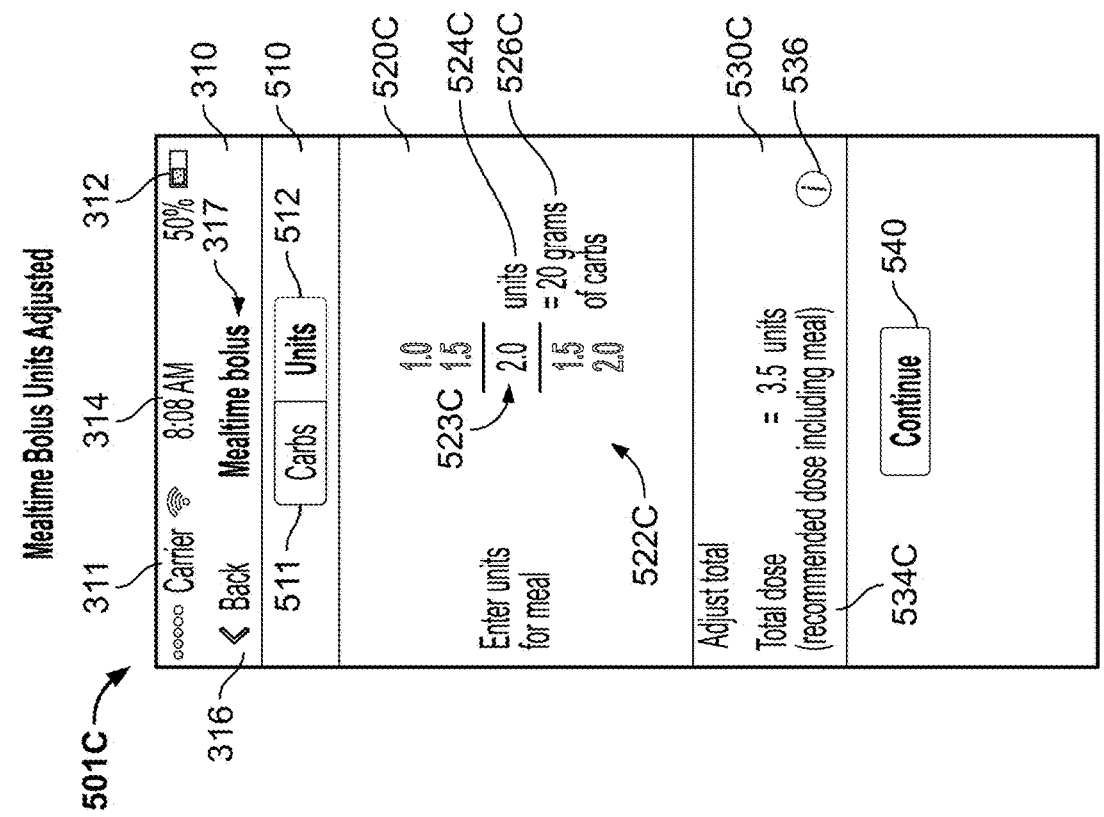
Figure 4G:
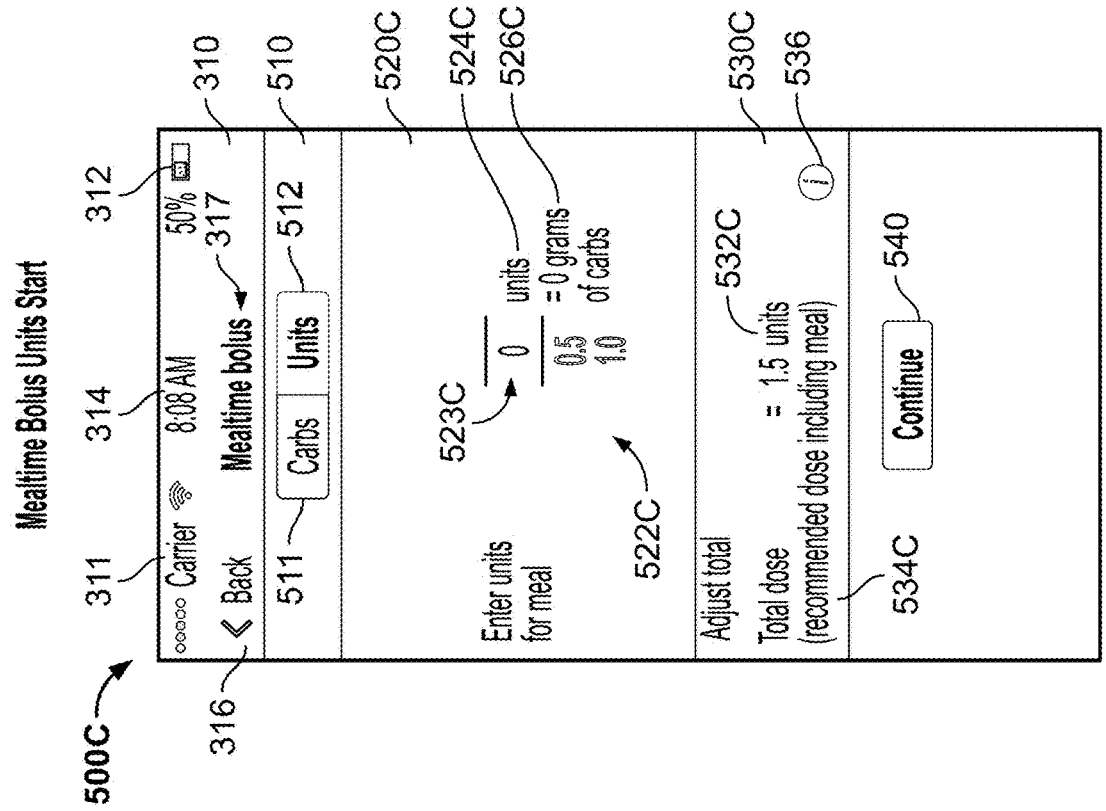

FIGS. 4G and 4H illustrate how the bolus calculator works if the user clicks on units control 512 to arrive at screen 500C and enters units 523C using a scroll wheel 522C. A conversion of the units 523C into a number of carbs 526C dynamically updates. Again, the units 524C is clearly displayed so that a user knows what is being entered. A total dose recommendation field 530C is also dynamically updated to display a calculated total dose 532C. Once a user hits continue button 540, the user is brought to a screen similar to screen 502A, as depicted in FIG. 4C, to allow the user to manually adjust and deliver an amount of insulin using similar functionality. In some cases, an alarm is scheduled for a predetermined number of minutes (e.g., 5 minutes) in the future as soon as the bolus screen is activated, and cleared upon the delivery of the insulin so that a user that inadvertently fails to deliver the bolus can be reminded that they may have intended to deliver a bolus. For example, this could be useful if the application is interrupted and the user is unsure if the bolus instruction was delivered to the insulin pump and/or forgets to finish to bolus delivery process. In some cases, the alarm can be set on pump controller.

DMS Operating Information

Referring back to FIG. 2, home screen 300 can include a CGM monitor field 360 and an insulin pump field 370 to display relevant information about whether these devices are properly connected and/or the mode of operation. For example, in order for a closed loop system to be in operation, the system requires proper access to the continuous glucose monitor (CGM) data, thus, indicating that the CGM Monitor is "ON" will assure the user that the DMS 10 is operating appropriately. If the user clicks on the CGM monitor field 360, the user can go to a screen where the user can adjust the continuous glucose monitor settings. In some cases, condition display 330 is only displayed in response to the CGM monitor being on. In some cases, when the CGM monitor is off, the system will display a warning in condition display 330 that the system cannot predict future glucose values because the CGM monitor is not operating.

In some cases, a user can select CGM monitor field 360 to make changes to the settings or to tell the DMS to stop using data from a paired continuous glucose monitor. For example, if a user suspects that the data from a paired continuous glucose monitor is inaccurate, a user can turn the CGM indicator to "OFF" so that the DMS will stop using glucose values from the continuous glucose monitor, which will stop any adjustments to basal insulin delivery rates from predetermined basal delivery rates. In some cases, the CGM monitor field 360 will be turned "OFF" during a warmup period after a new continuous glucose monitor sensor has been placed on the user.

Displaying the status of the insulin pump in field 370 is also useful to assure the user that the system is operating appropriately. In some cases, DMS can have a plurality of operating modes depending on the data available. For example, some modes may automate basal delivery rates based on CGM data in order to provide a closed loop system. Accordingly, displaying that automation is on for the insulin pump can assure the user that the DMS will automatically adjust basal delivery rates in order to control blood glucose levels.

Additional Data Entry Field

Referring again to FIG. 2, home screen 300 can also include navigation row 390 along the bottom of the device, which can display other user-selectable icons for less routine tasks. As discussed above, these tasks may be less frequent than mealtime boluses because they represent information that can be collected via wireless connections between a blood glucose meter 70, the pump assembly 15, and the continuous glucose monitor 50. As shown in FIG. 2, in some cases navigation row 390 can include a recording BG icon 392, recording outside insulin icon 394, and settings icon 396. Additional possible icons could include icons, for example, that allow a user to indicate exercise, sickness, sleep, and/or additional states that could impact blood glucose levels.

Figure 5:
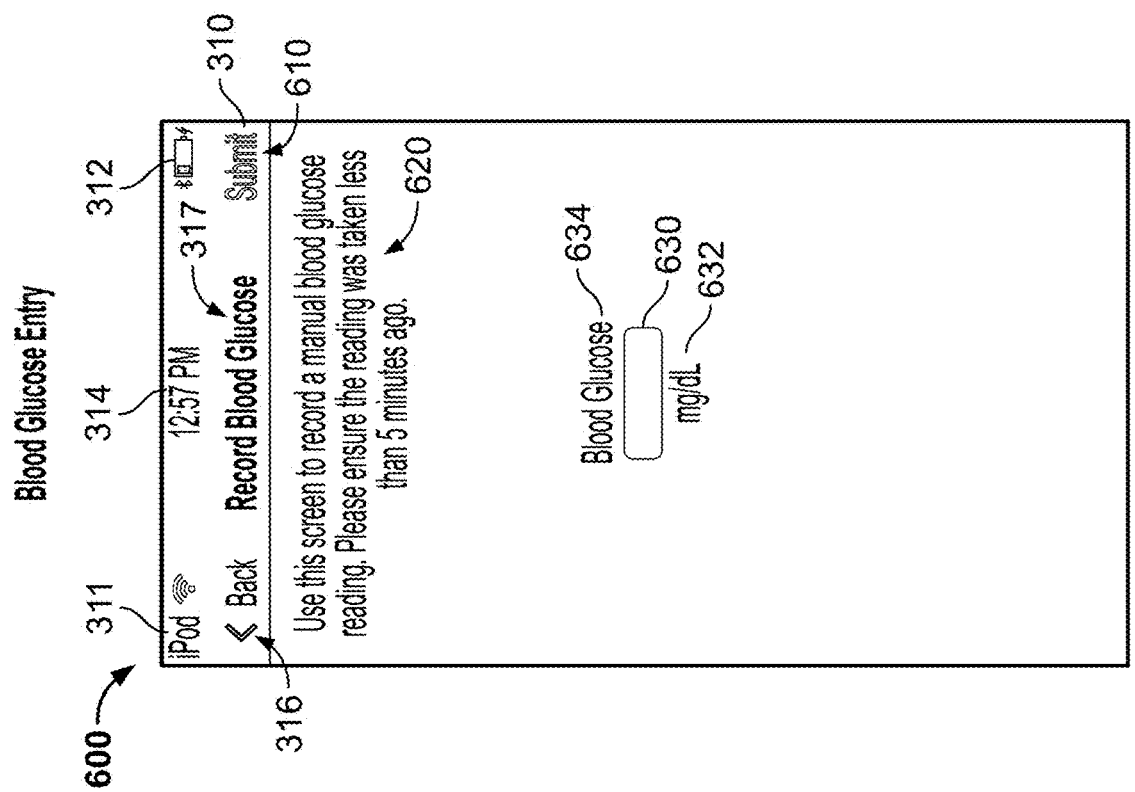
FIG. 5 illustrates an example user interface for entering a blood glucose value.

When a user selects icon 392 to input a blood glucose meter reading, a screen similar to screen 600, as depicted in FIG. 5, can appear. Screen 600 can include a header 310 similar to those discussed above, but also include a submit button 610. Screen 600 can include a warning about when the reading must have been taken 620, and an input field 630 for the blood glucose meter value. Screen 600 clearly includes a label 634 identifying the field as being for blood glucose and provides the units 632. In some cases, blood glucose measurement can be used to calibrate the continuous glucose monitor of the DMS. When a user clicks on field 630, a numerical keypad can appear to allow the user to enter a number and hit return. In some cases, screen 600 can pop up as part of completing the bolus calculator. As discussed above, DMS systems provided herein can include blood glucose meters in wireless communication with an insulin pump and/or a mobile computing device, thus the manual entry of blood glucose values may not be a typical action of a user.

Figure 6:
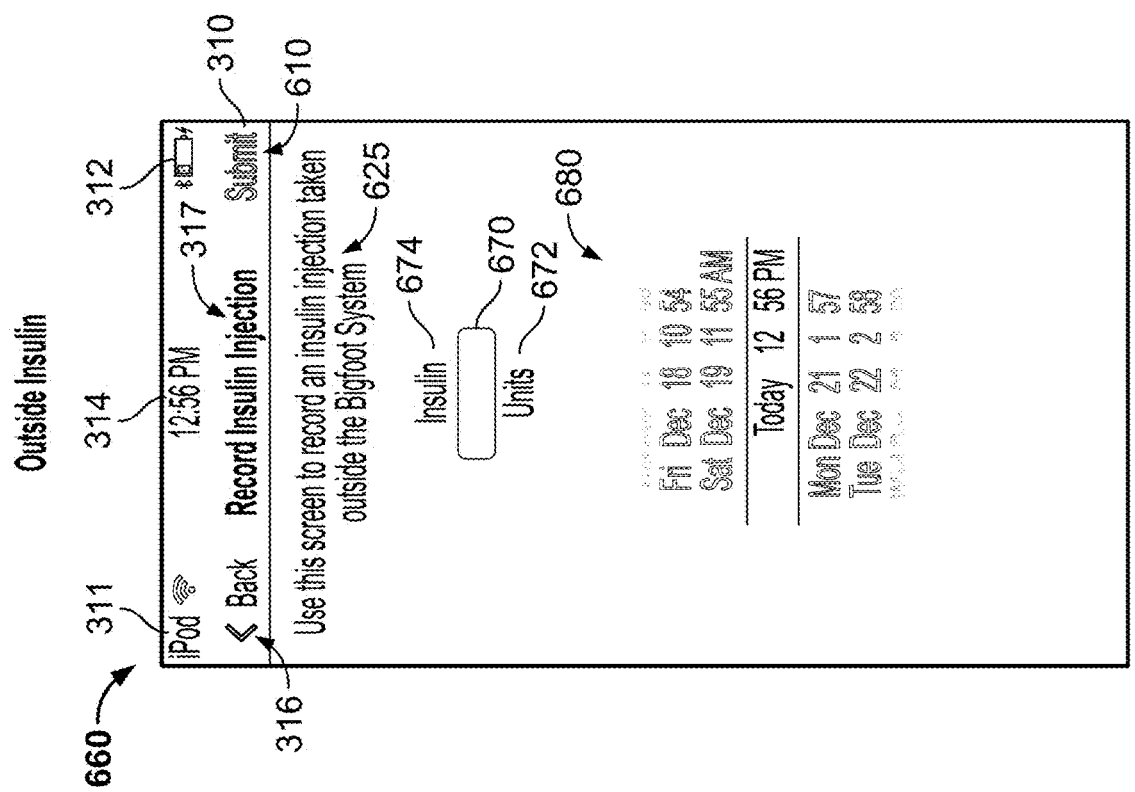
FIG. 6 illustrates an example user interface for reporting outside insulin.
Figure 7B:
Figure 7A:

When a user selects icon 394 to enter outside insulin, a screen similar to screen 660, as depicted in FIG. 6, can appear. Screen 660 can include a header 310 similar to those discussed above with a submit button 610, a warning about the insulin being insulin taken outside of the DMS system 625, and an input field 670 for entering a number of units 672 of outside insulin. Field 670 is clearly labeled as being insulin 674. Screen 660 also includes a time scrolling wheel 680 for a user to enter the time that the insulin was administered. In some cases, screens similar to screen 660 can allow for entry of different types of medication (e.g., glucagon), different types of insulin (e.g., slow acting insulin), and/or other information about how the medication was delivered.

When a user selects icon 396 (FIG. 2) to adjust settings, the user can adjust a number of other user settings, such as insulin sensitivity factors, carbohydrate to insulin ratios, baseline basal insulin delivery rates, and target glucose levels.

Maintenance Field

Home screen 300 also includes a maintenance field 380 adapted to indicate to a user if the user will be expected to conduct any maintenance tasks in the near future (e.g., in the next 24 hours) and/or whether the DMS has detected any need for immediate maintenance. For example, maintenance field 380 can indicate when an infusion set is due for replacement, when an infusion set should be changed, when disposable parts of a pumping assembly need to be replaced and/or when an insulin reservoir needs to be refilled, when the continuous glucose monitor sensor needs to be changed or moved to a new location on the body, or when a blood glucose measurement should be made to calibrate the continuous glucose monitor. In some cases, static indicators can indicate the approximate deadline for conducting routine maintenance, optionally with color indicators indicating the urgency of each maintenance task (e.g., red, yellow and green to indicate high, medium, and low urgency respectively). In some cases, maintenance field 380 can indicate that no maintenance tasks are required. In the cases that immediate maintenance is required, DMS 10 can provide an alarm (e.g., on the mobile computing device 60, pump assembly 15, or a combination thereof) to get the user to look at the user interface to learn about the required maintenance task. Maintenance field 380 is configured to reassure a user that system maintenance tasks are up-to-date, thus again reducing the cognitive burden on the user.

FIGS. 7A-7D depict pump maintenance user interfaces 701-704, which can be used when conducting pump maintenance. User interface 701 allows a user to select between conducting cannula fill operations and tube priming operations. User interface 702 confirms a cannula fill. User interface 703 provides options for a tubing prime operation. User interface 704 provides a warning that the tubing is about to be primed including a confirmation text box 774 over a shaded background 772.

Alarm Screen

FIG. 8 depicts an alarm screen 800 that includes a header 310 similar to those discussed above, and an alert field 810 and a text field 820. Alert field can be colored to indicate that an immediate action is needed. For example, field 810 can have a red background. Text field 820 can inform the user, potentially by name, that the DMS is taking a limited action but that the user may want to take additional action. An "OK" or "Okay" bottom can be present at the bottom of screen 800 for the user to acknowledge the alarm.

Alternative Home Screen and Navigation

FIGS. 9A and 9B depict an alternative dashboard having slide-out navigation to access various tasks. Dashboard 900 includes a graphical history display similar to that shown in FIG. 3A, discussed above, but uses this graphical display as part of a home screen. Dashboard 900 includes a header 910, similar to header 310 discussed above, that includes mobile computing device connection information, a mobile computing device power indicator, and a time of day. Beneath header 910, dashboard displays an estimate of the insulin on board (IOB) 930 and a most recent glucose measurement 932, and an arrow 933 showing a prediction of how blood glucose levels will change, similar to prediction arrow 335 discussed above. In some cases, dashboard 900 can include an alert icon 920 that appears if there is an alarm condition, which the user can select to learn details about the alert. Dashboard 900 further indicates when the most recent blood glucose measurement was taken. Chart 940 is similar to glucose value chart 450 discussed above, but can use different colors. Chart 950 is similar to charts 460 and 470 discussed above, but can include an overlay of the bars representing bolus deliveries and the step graph showing the basal rate. User-selectable icons along a bottom row 960 can allow a user to input a blood glucose measurement, icon 962, enter a meal for a bolus calculation, icon 962, and look at user settings, icon 964. Clicking on icon 962 can bring the user to the user interface of FIG. 5. Clicking on icon 964 can bring the user to the bolus calculator discussed above in relationship to FIGS. 4A-4G.

By clicking on navigation icon 970 in the upper left corner, a slide-out menu can appear, as shown as screen 901 in FIG. 9B. The navigation slide-out can include icons for recording outside insulin, changing device pairings, editing configurations, preforming insulin pump maintenance, preforming insulin infusion set maintenance, starting insulin delivery, starting a continuous glucose monitor sensor, changing the automation mode, and viewing the event history.

Exemplary Mobile Computing Device

Referring again to FIGS. 1, 1B, and 1C, mobile computing device 60 can communicate with the controller device 200 through a wireless and/or wired connection with the controller device 200 (e.g., via a Bluetooth wireless communication connection in this particular implementations). In some cases, mobile computing device 60 communicates wirelessly with other elements of the insulin delivery system 10. Mobile computing device 60 can be any of a variety of appropriate computing devices, such as a smartphone, a tablet computing device, a wearable computing device, a smartwatch, a fitness tracker, a laptop computer, a desktop computer, and/or other appropriate computing devices. In some cases where there is no computing device 200 that is part of a pump, the mobile computing device 60 can receive and log data from the other elements of insulin delivery system 10. In some cases, a user can input relevant data into mobile computing device 60. In some cases where a pump assembly 15 includes controller device 200, the mobile computing device 60 can receive and log data that is collected by the controller device 200, such as blood glucose readings, dosage delivery information, and also can receive user inputs (e.g., user-selected parameters to be stored on the controller device 200, user-confirmation of bolus dosages (described below), and others). In some cases, mobile computing device 60 can be used to transfer data from controller device 200 to the cloud. In some cases, the mobile computing device 60 provides a user interface (e.g., graphical user interface (GUI), speech-based user interface, motion-controlled user interface) through which users can provide information to control operation of the controller device 200 and the insulin delivery system 10. For example, the mobile computing device 60 can be a mobile computing device running a mobile app that communicates with the controller device 200 over short-range wireless connections (e.g., BLUETOOTH connection, Wi-Fi Direct connection) to provide status information for the insulin delivery system 10 and to allow a user to control operation of the insulin delivery system 10 (e.g., toggle between delivery modes, adjust settings, log food intake, confirm/modify/cancel bolus dosages, and the like).

Continuous Glucose Monitor

Continuous glucose monitor 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In some cases, the sensor shaft 56 can measure glucose or another analyte in interstitial fluid or in another fluid and correlate that to blood glucose levels. In response to the measurements made by the sensor shaft 56, continuous glucose monitor 50 can employ the wireless communication device 54 to transmit data to a corresponding wireless communication device 247 housed in the pump assembly 15. In some cases, the continuous glucose monitor 50 may include a circuit that permits sensor signals (e.g., data from the sensor shaft 56) to be communicated to the communication device 54. The communication device 54 can transfer the collected data to the controller device 200 (e.g., by wireless communication to the communication device 247). Alternatively, the continuous glucose monitor 50 can employ other methods of obtaining information indicative of a user's blood characteristics and transferring that information to the controller device 200. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. Invasive methods involving optical means of measuring glucose could also be added. In yet another example, the monitoring device can include an optical detection instrument that is inserted through the skin for measuring the user's glucose level. Furthermore, it should be understood that in some alternative implementations, the continuous glucose monitor 50 can be in communication with the controller device 200 or another computing device via a wired connection.

Blood Glucose Meter

DMS 10 may optionally communicate with blood glucose meter 70 in addition to (or as an alternative to) continuous glucose monitor 50. For example, one or more test strips (e.g., blood test strips) can be inserted into a strip reader portion of blood glucose meter 70 and then receive blood to be tested. In some cases, blood glucose meter 70 is configured to analyze the characteristics of the user's blood and to communicate (e.g., via a Bluetooth wireless communication connection) the information to the controller device 200. In some cases, a user can manually input a glucose meter reading. Blood glucose meter 70 can be manually operated by a user and may include an output subsystem (e.g., display, speaker) that can provide the user with blood glucose readings that can be subsequently entered into the controller or user interface (to collect the data from an unconnected BGM into the system). Blood glucose meter 70 may be configured to communicate data (e.g., blood glucose readings) obtained to the controller device 200 and/or other devices, such as the mobile computing device 60. Such communication can be over a wired and/or wireless connection, and the data can be used by the controller device 200 and/or the mobile computing device 60 to perform multiple delivery modes and/or a secondary feedback loop for the insulin delivery system 10.

External Insulin Delivery Devices

DMS 10 may include one or more external medication delivery devices 80 (e.g., syringe, an insulin pen, a smart syringe with device communication capabilities, or the like) through which additional medicine dosages (e.g., insulin, glucagon) can be manually administered to a user. In some cases, user interfaces provided herein allow users to input a medication, a dosage amount, and the timing so that a closed-loop control algorithm can account for the additional medication. In some cases, mobile computing device 60 can make a recommendation for an amount of insulin to be delivered using an external delivery device.

Pump Assembly

Referring again to FIG. 1, pump assembly 15 can include pump device 100 configured to removably attach to the controller device 200 in a manner that provides a secure fitting, an overall compact size, and a reliable electrical connection. Additional details about the particularly depicted pump assembly 15 are described in more detail below in connection with FIGS. 1B and 1C.

Pump assembly 15 can be pocket-sized so that the pump device 100 and controller device 200 can be worn in the user's pocket or in another portion of the user's clothing. In some circumstances, the user may desire to wear the pump assembly 15 in a more discrete manner. Accordingly, the user can pass the tube 147 from the pocket, under the user's clothing, and to the infusion site where the adhesive patch can be positioned. As such, the pump assembly 15 can be used to deliver medicine to the tissues or vasculature of the user in a portable, concealable, and discrete manner.

In some cases, the pump assembly 15 can be configured to adhere to the user's skin directly at the location in which the skin is penetrated for medicine infusion. For example, a rear surface of the pump device 100 can include a skin adhesive patch so that the pump device 100 can be physically adhered to the skin of the user at a particular location. In these cases, the cap device 130 can have a configuration in which medicine passes directly from the cap device 130 into an infusion set 146 that is penetrated into the user's skin. In some examples, the user can temporarily detach the controller device 200 (while the pump device 100 remains adhered to the skin) so as to view and interact with the user interface 220.

Referring now to FIG. 1B, the pump device 100 in this example includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (e.g., including a battery powered actuator, a gear system, a drive rod, and other items that are not shown in FIG. 5) that advances a plunger 125 in the fluid cartridge 120 so as to dispense fluid therefrom. In this example, the controller device 200 communicates with the pump device 100 to control the operation of the drive system. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device (having a new fluid cartridge) to the reusable controller device 200 for the dispensation of fluid from a new fluid cartridge. Accordingly, the user is permitted to reuse the controller device 200 (which may include complex or valuable electronics, as well as a rechargeable battery) while disposing of the relatively low-cost pump device 100 after each use. Such a pump assembly 15 can provide enhanced user safety as a new pump device (and drive system therein) is employed with each new fluid cartridge. Additional and/or alternative implementations of the controller device 200 are also possible, including magnetic drive turbine (MDT) monolithic architecture pumps and/or omnipods.

The pump assembly 15 can be a medical infusion pump assembly that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a fluid cartridge 120 in the form of a carpule that is preloaded with insulin or another medicine for use in the treatment of Diabetes (e.g., Exenatide (BYETTA, BYDUREON) and liraglutide (VICTOZA), SYMLIN, or others). Such a cartridge 120 may be supplied, for example, by Eli Lilly and Co. of Indianapolis, IN. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some cases, the pump device 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of the pump device 100. In some cases, the retainer wings can interfere with attempts to remove the fluid cartridge 120 from the pump device 100, thus ensuring that the pump device 100 will be discarded along with the fluid cartridge 120 after the fluid cartridge 120 is emptied, expired, or otherwise exhausted. In another example, the cap device 130 can be configured to irreversibly attach to the pump housing structure 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the fluid cartridge 120 is emptied, expired, or otherwise exhausted).

Still referring to FIG. 1B, the controller device 200 can be removably attached to the pump device 100 so that the two components are mechanically mounted to one another in a fixed relationship. In some cases, such a mechanical mounting can also form an electrical connection between the removable controller device 200 and the pump device 100 (for example, at electrical connector 118 of the pump device 100). For example, the controller device 200 can be in electrical communication with a portion of the drive system (show shown) of the pump device 100. In some cases, the pump device 100 can include a drive system that causes controlled dispensation of the medicine or other fluid from the cartridge 120. In some cases, the drive system incrementally advances a piston rod (not shown) longitudinally into the cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device 130 to the housing structure 110. Thus, when the pump device 100 and the controller device 200 are mechanically attached and thereby electrically connected, the controller device 200 communicates electronic control signals via a hardwire-connection (e.g., electrical contacts along connector 118 or the like) to the drive system or other components of the pump device 100. In response to the electrical control signals from the controller device 200, the drive system of the pump device 100 causes medicine to incrementally dispense from the fluid cartridge 120. Power signals, such as signals from a battery (not shown) of the controller device 200 and from the power source (not shown) of the pump device 100, may also be passed between the controller device 200 and the pump device 100.

Cap device 130 of the pump device 100 can be configured to mate with an infusion set 146. In general, the infusion set 146 can be a tubing system that connects the pump assembly 15 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 5) of the fluid cartridge 120 and the tube 147 of the infusion set 146.

Referring now to FIG. 1C, the controller device 200 (shown in an exploded view) houses a number of components that can be reused with a series of successive pump devices 100. In particular, the controller device 200 can include control circuitry 240 and a rechargeable battery pack 245, each arranged in the controller housing 210. The rechargeable battery pack 245 may provide electrical energy to components of the control circuitry 240, other components of the controller device (e.g., the display device 222 and other user interface components, sensors, or the like), or to components of the pump device 100. The control circuitry 240 may be configured to communicate control or power signals to the drive system of the pump device 100, or to receive power or feedback signals from the pump device 100.

The control circuitry 240 of the controller device 200 can include one or more microprocessors 241 configured to execute computer-readable instructions stored on one or more memory devices 242 so as to achieve any of the control operations described herein. At least one memory device 242 of the control circuitry may be configured to store a number of user-specific dosage parameters. Various user-specific dosage parameters can be automatically determined and/or updated by control operations implemented by the control circuitry 240 of the controller device 200. Additionally, the control circuitry 240 can cause the controller device 200 to periodically communicate the user-specific dosage parameters to the mobile computing device 60 for future use during operations by the mobile computing device 60 or for subsequent communication to cloud-based computer network.

In some cases, the control circuitry 240 can receive input data or other information from the mobile computing device 60 (e.g., via user input at the mobile computing device 60) and thereby cause the controller device 200 to output information to the mobile computing device 60 for display on the screen of the mobile computing device 60, such as settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The control circuitry 240 can be programmable to cause the control circuitry 240 to change any one of a number of settings or modes of operation for the insulin delivery system 10. In some cases, the control circuitry 240 can include a cable connector (e.g., a USB connection port or another data cable port) that is accessible on an external portion of the controller housing 210. As such, a cable can be connected to the control circuitry 240 to upload or download data or program settings to the control circuitry.

A number of implementations have been described. Nevertheless, it will be understood that various modifications may be made without departing from the spirit and scope of the invention. Accordingly, other implementations are within the scope of the following claims.

What is claimed is:

1. A mobile computing device for controlling a medical infusion pump system, the computing device comprising:
    a display screen of a smart phone or a tablet computer;
    one or more input controls manipulable by a user;
    one or more processors;
    a memory to store computer-readable instructions that, when executed by the one or more processors, enable the computing device to perform actions comprising:
        communicating with a controller of a medical infusion pump system to cause the medical infusion pump system to dispense medicine to a patient;
        receiving blood glucose level information for the patient, wherein the blood glucose level information is associated with one or more blood glucose measurement times;
        providing a graphic user interface formatted for the display screen of the smart phone or the tablet computer, wherein the graphical user interface includes:
            a blood glucose level chart presented at a first region of the graphical user interface, the blood glucose level chart depicting a series of blood glucose values included in the received blood glucose level information, the series of blood glucose values being aligned adjacent a first vertical axis and over a first time axis to reflect the times that the blood glucose values were measured; and
            an insulin delivery chart presented at a second region of the graphical user interface, the insulin delivery chart depicting (1) a first graph, presented at a first sub-region of the second region, showing a continuous line indicating basal delivery rates administered by the infusion pump system over time aligned adjacent a second vertical axis, and (2) a second graph, presented at a second sub-region of the second region, showing a series of insulin bolus indicators indicating times that insulin bolus deliveries were administered aligned adjacent a third vertical axis, respective areas defined by borders of bolus indicators representative of amounts of insulin bolus deliveries, wherein the first graph showing the continuous line indicating basal delivery rates and the second graph showing the series of insulin bolus indicators are aligned over a second time axis, wherein the first graph and the second graph presented at the first and second sub-regions, respectively, do not overlap, wherein the first and third vertical axis are aligned over the same portion of the second time axis,
    wherein the second time axis is distinct from the first time axis,
    wherein there is no spatial overlap between the blood glucose level chart and the insulin delivery chart,
    a current time; and
    a vertical line segment that intersects the first time axis and the second time axis respectively at points corresponding to the current time.

2. The computing device of claim 1, wherein the first time axis of the blood glucose level chart is positioned above the first graph showing the line indicating basal delivery rates and the second time axis of the insulin delivery chart is positioned below the graph showing the line indicating basal delivery rates.

3. The computing device of claim 1, wherein the first time axis of the blood glucose level chart is positioned above the series of insulin bolus indicators and the second time axis of the insulin delivery chart is positioned below at least a portion of each of the series of insulin bolus indicators.

4. The computing device of claim 1, wherein the first time axis of the blood glucose level chart is positioned above the insulin delivery chart.

5. The computing device of claim 1, wherein the first time axis of the blood glucose level chart and the second time axis of the insulin delivery chart are time-aligned within the graphic user interface.

6. The computing device of claim 5, wherein the graphic user interface further includes a current time line that passes through the first time axis of the blood glucose level chart and the second time axis of the insulin delivery chart to identify a current time with respect to the blood glucose level chart and the insulin delivery chart.

7. The computing device of claim 6, wherein the blood glucose level chart depicts a projection of future blood glucose values on a right side of the current time line; and wherein the insulin delivery chart depicts a scheduled future basal delivery rate on the right side of the current time line.

8. The computing device of claim 1, wherein:
    the received blood glucose level information comprises blood glucose level information measured by a continuous glucose monitor and blood glucose level information measured by a blood glucose meter; and
    the blood glucose level chart depicts a first series of blood glucose values measured by the continuous glucose monitor aligned over the first time axis to reflect the times that the blood glucose values in the first series of blood glucose values were measured by the continuous glucose monitor, and a second series of blood glucose values measured by the blood glucose meter aligned over the first time axis to reflect the times that the blood glucose values in the second series of blood glucose values were measured by the blood glucose meter.

9. The computing device of claim 8, wherein the first series of blood glucose values measured by the continuous glucose monitor are depicted using a first symbol and the second series of blood glucose values measured by the blood glucose meter are depicted using a second symbol, the second symbol being larger than the first symbol.

10. The computing device of claim 8, wherein the first series of blood glucose values measured by the continuous glucose monitor are depicted are depicted at a higher sampling rate than the second series of blood glucose values measured by the blood glucose meter.

11. The computing device of claim 8, wherein the first series of blood glucose values includes more blood glucose values than the second series of blood glucose values.

12. The computing device of claim 1, wherein the graphic user interface further comprises a display of a most recent glucose measurement that is distinct from the blood glucose level chart.

13. The computing device of claim 1, wherein the graphic user interface further comprises a display of an active insulin on board value.

14. The computing device of claim 1, wherein the graphic user interface further comprises an interactive control that allows the user to select an amount of time represented by the first time axis and the second time axis.

15. The computing device of claim 1, wherein the graphic user interface further comprises an indication of a current time.

16. A computer-implemented method, comprising:
communicating with a controller of a medical infusion pump system to cause the medical infusion pump system to dispense medicine to a patient;
receiving blood glucose level information for the patient, wherein the blood glucose level information is associated with one or more blood glucose measurement times;
providing a graphic user interface formatted for the display screen of a smart phone or a tablet computer, the graphic user interface including:
a blood glucose level chart, presented at a first region of the graphical user interface, the blood glucose level chart depicting a series of blood glucose values included in the received blood glucose level information, the series of blood glucose values being aligned adjacent a first vertical axis and over a first time axis to reflect the times that the blood glucose values were measured; and
an insulin delivery chart, presented at a second region of the graphical user interface, the insulin delivery chart, depicting (1) a graph, presented at a first sub-region of the second region, showing a continuous line indicating basal delivery rates administered by the infusion pump system over time aligned adjacent a second vertical axis, and (2) a second graph, presented at second sub-region of the second region, showing a series of insulin bolus indicators indicating times that insulin bolus deliveries were administered aligned adjacent a third vertical axis, respective areas defined by borders of bolus indicators representative of amounts of insulin bolus deliveries, wherein the first graph and the second graph presented at the first and second sub-regions, respectively, do not overlap, wherein the first and third vertical axis are aligned over the same portion of a second time axis,
wherein the graph showing the basal delivery rates and the series of insulin bolus indicators are aligned over the second time axis, wherein the second time axis is distinct from the first time axis,
wherein there is no overlap between the blood glucose level chart and the insulin delivery chart,
a current time; and
a vertical line segment that intersects the first time axis and the second time axis respectively at points corresponding to the current time.

17. The method of claim 16, wherein the first time axis of the blood glucose level chart is positioned above the first graph showing the continuous line indicating basal delivery rates and the second time axis of the insulin delivery chart is positioned below the graph showing basal delivery rates.

18. The method of claim 16, wherein the first time axis of the blood glucose level chart is positioned above the insulin delivery chart.

19. The method of claim 16, wherein the graphic user interface further includes a current time line that passes through the first time axis of the blood glucose level chart and the second time axis of the insulin delivery chart to identify a current time with respect to the blood glucose level chart and the insulin delivery chart; and
wherein the blood glucose level chart depicts a projection of future blood glucose values on a right side of the current time line; and wherein the insulin delivery chart depicts a scheduled future basal delivery rate on the right side of the current time line.

20. The method of claim 16, wherein:
the received blood glucose level information comprises blood glucose level information measured by a continuous glucose monitor and blood glucose level information measured by a blood glucose meter; and
the blood glucose level chart depicts a first series of blood glucose values measured by the continuous glucose monitor aligned over the first time axis to reflect the times that the blood glucose values in the first series of blood glucose values were measured by the continuous glucose monitor, and a second series of blood glucose values measured by the blood glucose meter aligned over the first time axis to reflect the times that the blood glucose values in the second series of blood glucose values were measured by the blood glucose meter.

21. The method of claim 16, wherein the graphic user interface further comprises a display of a most recent glucose measurement that is distinct from the blood glucose level chart.

22. A non-transitory computer-readable medium including instructions that, when executed by at least one processor, cause performance of operations that comprise:
communicating with a controller of a medical infusion pump system to cause the medical infusion pump system to dispense medicine to a patient;
receiving blood glucose level information for the patient, wherein the blood glucose level information is associated with one or more blood glucose measurement times;
providing a graphic user interface formatted for a display screen of a smart phone or tablet computer, the graphic user interface including:
a blood glucose level chart, presented at a first region of the graphical user interface, the blood glucose level chart, depicting a series of blood glucose values included in the received blood glucose level information, the series of blood glucose values being aligned adjacent a first vertical axis and over a first time axis to reflect the times that the blood glucose values were measured; and an insulin delivery chart, presented at a second region of the graphical user interface, the insulin delivery chart, depicting (1) a graph, presented at a first sub-region of the second region, showing a continuous line indicating basal delivery rates administered by the infusion pump system over time aligned adjacent a second vertical axis, and (2) a second graph, presented at a second sub-region of the second region, showing a series of insulin bolus indicators indicating times that insulin bolus deliveries were administered aligned adjacent a third vertical axis, respective areas defined by borders of bolus indicators representative of amounts of insulin bolus deliveries, wherein the first graph showing the continuous line indicating basal delivery rates and the second graph showing the series of insulin bolus indicators are aligned over a second time axis, wherein the first graph and the second graph presented at the first and second sub-regions, respectively, do not overlap, wherein the first and third vertical axis are aligned over the same portion of the second time axis, wherein the graph showing the basal delivery rates and the series of insulin bolus indicators are aligned over the second time axis, wherein the second time axis is distinct from the first time axis, wherein there is no overlap between the blood glucose level chart and the insulin delivery chart, a current time; and a vertical line segment that intersects the first time axis and the second time axis respectively at points corresponding to the current time.

23. The non-transitory computer-readable medium of claim 22, wherein the first time axis of the blood glucose level chart is positioned above the first graph showing the continuous line indicating basal delivery rates and the second time axis of the insulin delivery chart is positioned below the graph showing basal delivery rates.

24. The non-transitory computer-readable medium of claim 22, wherein the first time axis of the blood glucose level chart is positioned above the insulin delivery chart.

25. The non-transitory computer-readable medium of claim 22, wherein the graphic user interface further includes a current time line that passes through the first time axis of the blood glucose level chart and the second time axis of the insulin delivery chart to identify a current time with respect to the blood glucose level chart and the insulin delivery chart; and wherein the blood glucose level chart depicts a projection of future blood glucose values on a right side of the current time line; and wherein the insulin delivery chart depicts a scheduled future basal delivery rate on the right side of the current time line.

26. The non-transitory computer-readable medium of claim 22, wherein:

the received blood glucose level information comprises blood glucose level information measured by a continuous glucose monitor and blood glucose level information measured by a blood glucose meter; and the blood glucose level chart depicts a first series of blood glucose values measured by the continuous glucose monitor aligned over the first time axis to reflect the times that the blood glucose values in the first series of blood glucose values were measured by the continuous glucose monitor, and a second series of blood glucose values measured by the blood glucose meter aligned over the first time axis to reflect the times that the blood glucose values in the second series of blood glucose values were measured by the blood glucose meter.

27. The non-transitory computer-readable medium of claim 22, wherein the graphic user interface further comprises a display of a most recent glucose measurement that is distinct from the blood glucose level chart.

* * * * *

UNITED STATES PATENT AND TRADEMARK OFFICE
CERTIFICATE OF CORRECTION

PATENT NO. : 11,929,158 B2
APPLICATION NO. : 16/360751
DATED : March 12, 2024
INVENTOR(S) : Bryan Mazlish et al.

It is certified that error appears in the above-identified patent and that said Letters Patent is hereby corrected as shown below:

In the Claims

Claim 8, Column 22, Line 67, change "glucose monitor, and" to --glucose monitor; and--

Signed and Sealed this
Twenty-first Day of May, 2024

Katherine Kelly Vidal
*Director of the United States Patent and Trademark Office*